United States Patent

Inui et al.

Patent Number: 5,889,095
Date of Patent: Mar. 30, 1999

[54] PHOSPHITES, PROCESS FOR PRODUCING THE SAME AND THEIR USE

[75] Inventors: Naoki Inui, Nara; Taketoshi Kikuchi; Kanako Fukuda, both of Osaka; Takashi Sanada, Chiba, all of Japan

[73] Assignee: Sumitomo Chemical Company, Ltd., Osaka, Japan

[21] Appl. No.: 905,329

[22] Filed: Aug. 4, 1997

[30] Foreign Application Priority Data

Aug. 5, 1996 [JP] Japan .................................. 8-205738

[51] Int. Cl.⁶ .............................. C08K 5/49; C07C 69/76
[52] U.S. Cl. ............................... 524/117; 558/85; 558/95
[58] Field of Search ............................ 524/117; 558/85, 558/95

[56] References Cited

U.S. PATENT DOCUMENTS

| | | | |
|---|---|---|---|
| 4,132,702 | 1/1979 | Schmidt et al. | 524/117 |
| 4,182,704 | 1/1980 | Spivack | 524/117 |
| 4,348,495 | 9/1982 | Buysch et al. | 524/117 |
| 5,576,365 | 11/1996 | Fukuda et al. | |

FOREIGN PATENT DOCUMENTS

| | | |
|---|---|---|
| 2119319 A | 9/1994 | Canada . |
| 0767175 A | 4/1997 | European Pat. Off. . |
| 05086084 A | 4/1993 | Japan . |
| 08208885 A | 8/1996 | Japan . |
| 09124673 A | 5/1997 | Japan . |
| 09124674 A | 5/1997 | Japan . |

*Primary Examiner*—Veronica P. Hoke
*Attorney, Agent, or Firm*—IP Group of Pillsbury Madison & Sutro, LLP

[57] ABSTRACT

A phosphite stabilizer for organic material is represented by the formula (1):

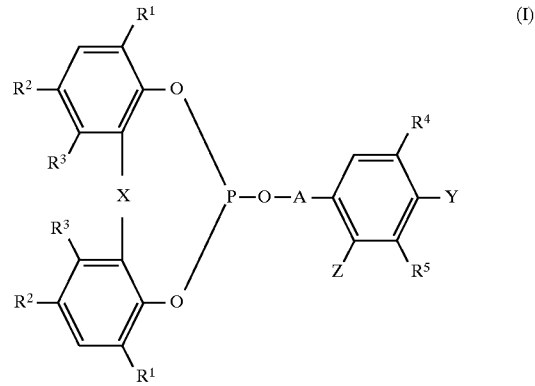

wherein $R^1$, $R^2$, $R^4$ and $R^5$ is hydrogen, alkyl, cycloalkyl, alkyl, cycloalkyl, aralkyl or phenyl; R is hydrogen or alkyl; X is a direct bond, sulfur atom or a —$CHR^6$ group in which $R^6$ represents hydrogen, alkyl or cycloalkyl; A is an alkylene group having 2 to 8 carbon atoms or *—$COR^7$— in which $R^7$ is a direct bond or alkyl group, and * represents the bond to the oxygen atom of the phenoxy radical; and one of Y and Z represents a hydroxyl group, an alkoxy group or an aralkoxy group and the other one represents atom or an alkyl group.

11 Claims, No Drawings

PHOSPHITES, PROCESS FOR PRODUCING THE SAME AND THEIR USE

FIELD OF THE INVENTION

The present invention relates to novel phosphites, a process for producing the same and their use as a stabilizer for organic material.

BACKGROUND OF THE INVENTION

It has been known that organic materials such as thermoplastic resin, thermosetting resin, natural or synthetic rubber, mineral oil, lubricating oil, adhesive or paint are deteriorated by an action of heat, oxygen, etc. on their production, processing and use to cause lowering of the strength of the organic materials, change in flow properties, coloring, deterioration of surface physical properties due to a phenomenon such as molecular cleavage or molecular closslinking. These deterioration result in decrease of their commercial value. It has hitherto been known that the organic material is stabilized by various phenol and phosphorous antioxidants, and these antioxidants have been used for solving problems of heat deterioration and oxidation deterioration.

As the phosphorous antioxidant, for example, distearyl pentaerythritol diphosphite, tris(2,4-di-t-butylphenyl) phosphite, bis(2,4-di-t-butylphenyl)pentaerythritol diphosphite and bis(2,6-di-t-butyl-4-methylphenyl)pentaerythritol diphosphite are used.

However, the stabilizing effect to heat deterioration and oxidation deterioration of these known phosphorous antioxidants is insufficient. For example, bis(2,4-di-t-butylphenyl)pentaerythritol diphosphite and the like had a problem that, since it is liable to be hydrolyzed, the hydrolysis occurs on storage to cause scattering in processing stability and an organic material having stable quality can not be obtained, and a problem that a metal in a processing machine is corroded by phosphites produced as a result of the hydrolysis.

On the other hand, for solving the problem of the known phosphorous antioxidants, the present inventors have already suggested a cyclic phosphite having a carbonyloxyalkylene group, such as 2,10-dimethyl-4,8-di-t-butyl-6-{2-[3-(3-t-butyl-4-hydroxy-5-methylphenyl) propionyloxy]ethoxy}-12H-dibenzo[d,g][1,3,2]dioxaphosphosine. (JP-A-5-86084).

However, although the stabilizing effect of this cyclic phosphite to heat deterioration and oxidization deterioration was improved, this improvement was still not satisfactory. The coloring resistance of this cyclic phosphite to a NOx gas is not sufficient either. Therefore, more improvement has been desired.

The present inventors have produces various cyclic phosphites and studied intensively so as to develop the phosphorous compound which hardly cause the hydrolysis and the stabilizing effect to heat and oxidization deterioration and NOx gas has been improved. As a result, it has been found that specific cyclic phosphites having a carbonyl group or an alkylene group in place of the carbonyloxyalkylene group shows excellent stabilizing effect. Thus, the present invention has been accomplished.

SUMMARY OF THE INVENTION

The present invention provides phosphites represented by the formula (I):

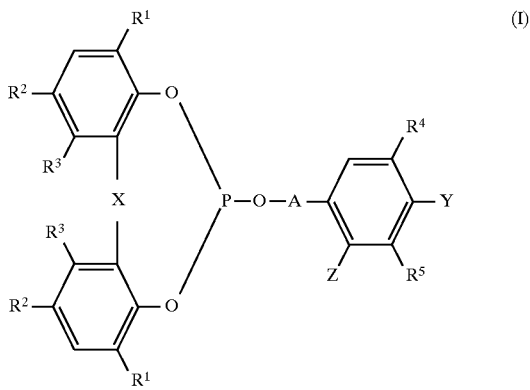

wherein $R^1$, $R^2$, $R^4$ and $R^5$ each independently represent hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group; $R^3$ represents hydrogen atom or an alkyl group having 1 to 8 carbon atoms; X represents a direct bond, sulfur atom, or a —$CHR^6$ group in which $R^6$ represents hydrogen atom, an alkyl group having 1 to 8 carbon atoms or a cycloalkyl group having 5 to 8 carbon atoms; A represents an alkylene group having 2 to 8 carbon atoms or a *—$COR^7$— group in which $R^7$ represents a direct bond or an alkylene group having 1 to 8 carbon atoms, and * represents the bond to the oxygen; and one of Y and Z represents a hydroxyl group, an alkoxy group having 1 to 8 carbon atoms or an aralkyloxy group having 7 to 12 carbon atoms and the other one represents hydrogen atom or an alkyl group having 1 to 8 carbon atoms.

The present invention also provides a process for producing the phosphites of formula (I) and their use.

DETAILED DESCRIPTION OF THE INVENTION

In the phosphites of formula (I) of the present invention, substituents $R^1$, $R^2$, $R^4$ and $R^5$ independently represent hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group.

It is preferred that $R^1$, $R^2$ and $R^4$ are an alkyl group having 1 to 8 carbon atoms, a cycloalkyl group having 5 to 8 carbon atoms or an alkylcycloalkyl group having 6 to 12 carbon atoms. It is preferred that $R^5$ is a hydrogen atom, an alkyl group having 1 to 8 carbon atoms or a cycloalkyl group having 5 to 8 carbon atoms.

Typical examples of the alkyl group having 1 to 8 carbon atoms include methyl, ethyl, n-propyl, i-propyl, n-butyl, i-butyl, sec-butyl, t-butyl, t-pentyl, i-octyl, t-octyl and 2-ethylhexyl.

Typical examples of the cycloalkyl group having 5 to 8 carbon atoms include cyclopentyl, cyclohexyl, cycloheptyl and cyclooctyl.

Typical examples of the alkylcycloalkyl group having 6 to 12 carbon atoms include 1-methylcyclopentyl, 1-methylcyclohexyl and 1-methyl-4-i-propylcyclohexyl.

Typical examples of the aralkyl group having 7 to 12 carbon atoms include benzyl, α-methylbenzyl and α,α-dimethylbenzyl.

It is particularly preferred that $R^1$ and $R^4$ are a t-alkyl group such as t-butyl, t-pentyl and t-octyl, cyclohexyl or i-methylcyclohexyl. $R^2$ is preferably an alkyl group having 1 to 5 carbon atoms, such as methyl, ethyl, n-propyl, i-propyl, n-butyl, i-butyl, sec-butyl, t-butyl, and t-pentyl, particularly methyl, t-butyl or t-pentyl. $R^5$ is preferably hydrogen atom or an alkyl group having 1 to 5 carbon atoms, such as methyl, ethyl, n-propyl, i-propyl, n-butyl, i-butyl, sec-butyl, t-butyl and t-pentyl.

The substituent $R^3$ represents hydrogen atom or an alkyl group having 1 to 8 carbon atoms. Examples of the alkyl group having 1 to 8 carbon atoms include methyl, ethyl, n-propyl, i-propyl, n-butyl, i-butyl, sec-butyl, t-butyl, t-pentyl, i-octyl, t-octyl and 2-ethylhexyl. It is preferably that $R^3$ is hydrogen atom or an alkyl group having 1 to 5 carbon atoms, particularly hydrogen atom or a methyl group.

The substituent X represents a direct bond, sulfur atom, or a methylene group which may optionally be substituted with alkyl having 1 to 8 carbon atoms or cycloalkyl having 5 to 8 carbon atoms.

Examples of the alkyl having 1 to 8 carbon atoms and cycloalkyl having 5 to 8 carbon atoms, with which the methylene group is substituted, include methyl, ethyl, n-propyl, i-propyl, n-butyl, i-butyl, sec-butyl, t-butyl, t-pentyl, i-octyl, t-octyl, 2-ethylhexyl, cyclopentyl, cyclohexyl, cycloheptyl and cyclooctyl.

X is preferably a direct bond, a methylene group or a methylene group substituted with methyl, ethyl, n-propyl, i-propyl, n-butyl, i-butyl, t-butyl or the like.

The substituent A represents an alkylene group having 2 to 8 carbon atoms or a *—$COR^7$— group in which $R^7$ represents a direct bond or an alkylene group having 1 to 8 carbon atoms, and * represents the bond to the oxygen, that is, indicated that the carbonyl group of *—$COR^7$— group is bonded to oxygen of the phosphite.

Typical examples of the alkylene group having 2 to 8 carbon atoms include ethylene, propylene, butylene, pentamethylene, hexamethylene, octamethylene and 2,2-dimethyl-1,3-propylene. Among them, propylene is preferred.

Typical examples of the alkylene group having 1 to 8 carbon atoms as $R^7$ include methylene, ethylene, propylene, butylene, pentamethylene, hexamethylene, octamethylene and 2,2-dimethyl-1,3-propylene. It is preferred that $R^7$ is a direct bond, ethylene or the like.

One of Y and Z represents a hydroxy group, an alkoxy group having 1 to 8 carbon atoms or an aralkyloxy group having 7 to 12 carbon atoms, and the other one represents hydrogen atom or an alkyl group having 1 to 8 carbon atoms.

Examples of the alkyl group having 1 to 8 carbon atoms include methyl, ethyl, n-propyl, i-propyl, n-butyl, i-butyl, sec-butyl, t-butyl, t-pentyl, i-octyl, t-octyl, and 2-ethylhexyl. Examples of the alkoxy group having 1 to 8 carbon atoms include alkoxy group whose alkyl moiety is methyl, ethyl, n-propyl, i-propyl, n-butyl, i-butyl, sec-butyl, t-butyl, t-pentyl, i-octyl, t-octyl or 2-ethylhexyl. Examples of the aralkyloxy group having 7 to 12 carbon atoms include an aralkyloxy group whose aralkyl moiety is benzyl, α-methylbenzyl or α,α-dimethylbenzyl.

The phosphites represented by the above formula (I) can be produced, for example, by reacting bisphenols represented by the general formula (II):

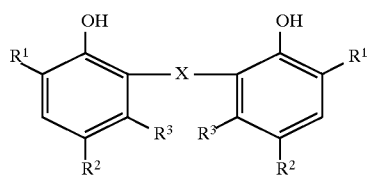

wherein $R^1$, $R^2$, $R^3$ and X are the same as defined above and phosphorous trihalide with an hydroxyl compound represented by the general formula (III):

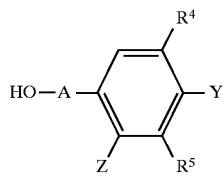

wherein $R^4$, $R^5$, A, Y, and Z are the same as defined above.

Examples of the phosphorous trihalide include phosphorous trichloride and phosphorous tribromide. Particularly, phosphorous trichloride is preferred.

In the reaction, the reaction can also be promoted, for example, by the copresence of a dehydrohalogenation agent such as amines, pyridines, pyrrolidines and amides or a hydroxide of alkaline metal or alkaline earth metal.

The amines may be a primary amine, a secondary amine or a teriary amine. Examples of the amines include t-butylamine, t-pentylamine, t-hexylamine, t-octylamine, di-t-butylamine, di-t-pentylamine, di-t-hexylamine, di-t-octylamine, trimethylamine, triethylamine, N,N-dimethylaniline and N,N-diethylaniline. Among them, triethylamine is preferred.

Examples of the pyridines include pyridine and picoline. Among them, pydrine is preferred. Examples of the pyrrolidines include 1-methyl-2-pyrrolidine.

Examples of the amides include N,N-dimethylformamide and N,N-dimethylacetylamide. Among them, N,N-dimethylformamide is preferred.

Examples of the hydroxide of the aklaline metal or alkaline earth metal include sodium hydroxide and calcium hydroxide. Among them, sodium hydroxide is preferred.

The reaction is normally conducted in an organic solvent. The organic solvent may be any one which does not inhibit the reaction, and is not specifically limited. Examples thereof include aromatic hydrocarbon, aliphatic hydrocarbon, oxygen-containing hydrocarbon and halogenated hydrocarbon.

Examples of the aromatic hydrocarbon includes benzene, toluene, xylene and ethylbenzene. Examples of the aliphatic hydrocarbon includes n-hexane, n-heptane and n-octane. Examples of the oxygen-containing hydrocarbon includes diethyl ether, di-butyl ether, tetrahydrofuran and 1,4-dioxane. Examples of the halogenated hydrocarbon includes chloroform, carbon tetrachloride, monochlorobenzene, dichloromethane, 1,2-dichloroethane and dichlorobenzene.

Among them, toluene, xylene, n-hexane, n-heptane, diethyl ether, tetrahydrofuran, 1,4-dioxane, chloroform and dichloromethane are preferably used.

As the reaction method, there is normally used a two-state reaction method of reacting the bisphenols (II) with phosphorous trihalide to form an intermediate and then reacting the intermediate with the hydroxy compound (III).

In the two-state reaction method, phosphorous trihalide is preferably used in an amount of about 1 to 1.1 mol, more preferably about 1 to 1.05 mol, per a mol of the bisphenols (II). The dehydrohalogenation agent is preferably used in an amount of about 0.05 to 2.4 mol, more preferably about 2 to 2.1 mol, per a mol of phosphorous trihalide.

The reaction between the bisphenols (II) and phosphorous trihalide is normally carried out at about 0° to 200° C. It is considered that an intermediate, halogenophosphite, is produced by this reaction. The intermediate may be applied to the reaction between the intermediate and the hydroxy compound (III) after being isolated but is normally applied to the following reaction without being isolated, i.e. as the reaction mixture.

In the reaction between the intermediate and the hydroxyl compound (III), the hydroxyl compound (III) are normally used in an amount of about 1 to 1.1 mol per a mole of the bisphenols (II).

In this reaction, the dehydrohalogenation agent can also be used. The amount of the dehydrohalogenation agent is preferably about 0.05 to 1.2 mol per mol of the hydroxyl compound (III). When using the excess dehydrohalogenation agent in the reaction of first stage, the amount of the dehydrohalogenation agent to be added in the second stage is normally calculated taking the amount of the remaining dehydrohalogenation agent into consideration.

The reaction is normally carried out at the temperature of 0° to 200° C.

After the completion of the reaction, the phosphites (I) of the present invention can be obtained by removing the hydrogen halogenide of the dehydrohalogenation agent, when using the dehydrohalogenation agent, and the solvent, followed by subjecting to a suitable post treatment such as crystallization and column chromatography.

The bispnenols (II) as a raw material of the phosphites (I) can also be produced by condensing aklylphenols according to a known method, for example, methods described in JP-A-52-122350, U.S. Pat. No. 2,538,355 or JP-A-2-47451. Commercially available bisphenols (II) can also be used.

Examples of the bisphenols (II) include 2,2'-methylenebis(4-methyl-6-t-butylphenol), 2,2'-methylenebis(4-ethyl-6-t-butylphenol), 2,2'-methylenebis(4-n-propyl-6-t-butylphenol), 2,2'-methylenebis(4-i-propyl-6-t-butylphenol), 2,2'-methylenebis(4-n-butyl-6-t-butylphenol), 2,2'-methylenebis(4-i-butyl-6-t-butylphenol), 2,2'-methylenebis(4,6-di-t-butylphenol), 2,2'-methylenebis(4-t-pentyl- 6-t-butylphenol), 2,2'-methylenebis(4-nonyl-6-t-butylphenol), 2,2'-methylenebis(4-t-octyl-6-t-butylphenyl), 2,2'-methylenebis(4-methyl-6-t-pentylphenol), 2,2'-methylenebis(4-methyl-6-cyclohexylphenol), 2,2'-methylenebis[4-methyl-6-(α-methylcyclohexyl)phenol)], 2,2'-methylenebis(4-methyl-6-t-nonylphenol), 2,2'-methylenebis(4-methyl-6-t-octylphenol), 2,2'-methylenebis(4,6-di-t-pentylphenol), 2,2'-methylenebis[4-nonyl-6-(α-methylbenzyl)phenol], 2,2'-methylenebis[4-nonyl-6-(α,α-dimethylbenzyl)phenol], 2,2'-ethylidenebis(4-methyl-6-butylphenol), 2,2'-ethylidenebis(4-ethyl-6-t-butylphenol), 2,2'-ethylidenebis(4-n-propyl-6-t-butylphenol), 2,2'-ethylidenebis(4-i-propyl-6-t-butylphenol), 2,2'-ethylidenebis(4-n-butyl-6-t-butylphenol), 2,2'-ethylidenebis(4-i-butyl-6-t-butylphenol), 2,2'-ethylidenebis(4,6-di-t-butylphenol), 2,2'-ethylidenebis(4-t-pentyl-6-t-butylphenol), 2,2'-ethylidenebis(4-nonyl-6-t-butylphenol), 2,2'-ethylidenebis(4-t-octyl-6-t-butylphenol), 2,2'-ethylidenebis(4-methyl-6-t-pentylphenol), 2,2'-ethylidenebis(4-methyl-6-cyclohexylphenol), 2,2'-ethylidenebis[4-methyl-6-(α-methylcyclohexyl)phenol)], 2,2'-ethylidenebis(4-methyl-6-nonylphenol), 2,2'-ethylidenebis(4-methyl-6-t-octylphenol), 2,2'-ethylidenebis(4,6-di-t-pentylphenol), 2,2'-ethylidenebis[4-nonyl-6-(α-methylbenzyl)phenol], 2,2'-ethylidenebis[4-nonyl-6-(α,α-dimethylbenzyl)phenol], 2,2'-propylidenebis(4-methyl-6-t-butylphenol), 2,2'-propylidenebis(4-ethyl-6-t-butylphenol), 2,2'-propylidenebis(4-n-propyl-6-t-butylphenol), 2,2'-propylidenebis(4-i-propyl-6-t-butylphenol), 2,2'-propylidenebis(4-n-butyl-6-t-butylphenol), 2,2'-propylidenebis(4-i-butyl-6-t-butylphenol), 2,2'-propylidenebis(4,6-di-t-butylphenol), 2,2'-propylidenebis(4-t-pentyl-6-t-butylphenol), 2,2'-propylidenebis(4-nonyl-6-t-butylphenol), 2,2'-propylidenebis(4-t-octyl-6-t-butylphenol), 2,2'-propylidenebis(4-methyl-6-t-pentylphenol), 2,2'-propylidenebis(4-methyl-6-cyclohexylphenol), 2,2'-propylidenebis[4-methyl-6-(α-methylcyclohexyl)phenol)], 2,2'-propylidenebis(4-methyl-6-nonylphenol), 2,2'-propylidenebis(4-methyl-6-t-octylphenol), 2,2'-propylidenebis(4,6-di-t-pentylphenol), 2,2'-propylidenebis[4-nonyl-6-(α-methylbenzyl)phenol], 2,2'-propylidenebis[4-nonyl-6-(α,α-dimethylbenzyl)phenol], 2,2'-butylidenebis(4-methyl-6-t-butylphenol), 2,2'-butylidenebis(4-ethyl-6-t-butylphenol), 2,2'-butylidenebis(4,6-di-t-butylphenol), 2,2'-butylidenebis(4-methyl-6-cyclohexylphenol), 2,2'-butylidenebis[4-methyl-6-(α-methylcyclohexyl)phenol)], 2,2'-butylidenebis(4,6-di-t-pentylphenol), 2,2'-i-butylidenebis(4-methyl-6-t-butylphenol), 2,2'-i-butylidenebis(4-ethyl-6-t-butylphenol), 2,2'-i-butylidenebis(4,6-di-t-butylphenol), 2,2'-i-butylidenebis(4-methyl-6-cyclohexylphenol), 2,2'-i-butylidenebis[4-methyl-6-(α-methylcyclohexyl)phenol)], 2,2'-i-butylidenebis(4,6-di-t-pentylphenol), 2,2'-i-pentylidenebis(4-methyl-6-t-butylphenol), 2,2'-i-pentylidenebis(4-ethyl-6-t-butylphenol), 2,2'-i-pentylidenebis(4,6-di-t-butylphenol), 2,2'-i-pentylidenebis(4-methyl-6-cyclohexylphenol), 2,2'-pentylidenebis[4-methyl-6-(α-methylcyclohexy)phenol], 2,2'-pentylidenebis(4,6-di-t-pentylphenol), biphenyl-2,2'-diol, 3,3',5,5'-tetra-t-butylbiphenyl-2,2'-diol and 1,1'binaphthyl-2,2'-diol.

When A is alkylene having 2 to 8 carbon atoms, the hydroxy compound (III) as another raw material can be produced, for example, by reducing a corresponding phenylcarboxylic acid or esters thereof, benzaldehydes or the like according to a known method.

Examples of a reducing agent include aluminum lithium hydride, aluminum sodium hydride, lithium borohydride, sodium borohydride, calcium borohydride, aluminum sodium triethoxyhydride, sodium triacetoxyborohydride, tributyltin hydride, 9-BBN-Pyridine, boron trihydride, sodium/ammonia in the co-presence of alcohol, lithium/ammonia in the co-presence of alcohol and di-isobutylaluminum hydride.

Typical examples of the hydroxy compound (III) when A is alkylene having 2 to 8 carbon atoms include 2-(3-t-butyl-4-hydroxyphenyl)ethanol, 2-(3-t-pentyl-4-hydroxyphenyl)ethanol, 2-(3-t-octyl-4-hydroxyphenyl)ethanol, 2-(3-cyclohexyl-4-hydroxyphenyl)ethanol, 2-[3-(1-methylcyclohexyl)-4-hydroxyphenyl]ethanol, 2-(3-t-butyl-4-hydroxy-5-methylphenyl)ethanol, 2-(3-t-pentyl-4-hydroxy-5-methylphenyl)ethanol, 2-(3-t-octyl-4-hydroxy-5-methylphenyl)ethanol, 2(3-cyclohexyl-4-hydroxy-5-methylphenyl)ethanol, 2-[3-(1-methylcyclohexyl)-4-hydroxy-5-methylphenyl)ethanol, 2-(3-t-butyl-4-hydroxy-5-ethylphenyl)ethanol, 2-(3-t-pentyl-4-hydroxy-5-ethylphenyl)ethanol, 2-(3-t-octyl-4-hydroxy-5-ethylphenyl) ethanol, 2-(3-cyclohexyl-4-hydroxy-5-ethylphenyl)ethanol, 2-[3-(1-methylcyclohexyl)-4-hydroxy-5-ethylphenyl)ethanol, 2-(3,5-di-t-butyl-4-hydroxyphenyl)ethanol, 2-(3-t-pentyl-4-hydroxy-5-t-butylphenyl)ethanol, 2-(3-t-octyl-4-hydroxy-5-t-butylphenyl)ethanol, 2-(3-cyclohexyl-4-hydroxy-5-t-butylphenyl)ethanol, 2-[3-(1- methylcyclohexyl)-4-hydroxy-5-butylphenyl)ethanol, 2-(3-t-butyl-4-methoxyphenyl)ethanol, 2-(3-t-pentyl-4-methoxyphenyl)ethanol, 2-(3-t-octyl-4-methoxyphenyl) ethanol, 2-(3-cyclohexyl-4-methoxyphenyl)ethanol, 2-[3-(1-methylcyclohexyl)-4-methoxyphenyl]ethanol, 2-(3-t-butyl-4-methoxy-5-methylphenyl)ethanol, 2-(3-t-pentyl-4-methoxy-5-methylphenyl)ethanol, 2-(3-t-octyl-4-methoxy-5-methylphenyl)ethanol, 2-(3-cyclohexyl-4-methoxy-5-methylphenyl)ethanol, 2-[3-(1-methylcyclohexyl)-4-methoxy-5-methylphenyl)ethanol, 2-(3-t-butyl-4-methoxy-5-ethylphenyl)ethanol, 2-(3-t-pentyl-4-methoxy-5-ethylphenyl)ethanol, 2-(3-t-octyl-4-methoxy-5-ethylphenyl) ethanol, 2-(3-cyclohexyl-4-methoxy-5-ethylphenyl)ethanol, 2-[3-(1-methylcyclohexyl)-4-methoxy-5-ethylphenyl) ethanol, 2-(3,5-di-t-butyl-4-methoxyphenyl)ethanol, 2-(3-t-pentyl-4-methoxy-5-t-butylphenyl)ethanol, 2-(3-t-octyl-4-methoxy-5-t-butylphenyl)ethanol, 2-(3-cyclohexyl-4-methoxy-5-t-butylphenyl)ethanol, 2-[3-(1-methylcyclohexyl)-4-methoxy-5-butylphenyl)ethanol, 3-(3-t-butyl-2-hydroxyphenyl)propanol, 3-(3-t-butyl-4-hydroxyphenyl)propanol, 3-(5-t-butyl-2-hydroxyphenyl) propanol, 3-(3-t-pentyl-4-hydroxyphenyl)propanol, 3-(3-t-octyl-4-hydroxyphenyl)propanol, 3-(3-cyclohexyl-4-hydroxyphenyl)propanol, 3-[3-(1-methylcyclohexyl)-4-hydroxyphenyl)propanol, 3-(3-t-butyl-2-hydroxy-5-methylphenyl)propanol, 3-(3-t-butyl-4-hydroxy-5-methylphenyl)propanol, 3-(3-t-butyl-4-hydroxy-5-methylphenyl)propanol, 3-(5-t-butyl-2-hydroxy-3-methylphenyl)propanol, 3-(3-t-pentyl-4-hydroxy-5-methylphenyl)propanol, 3-(3-t-octyl-4-hydroxy-5-methylphenyl)propanol, 3-(3-cyclohexyl-4-hydroxy-5-methylphenyl)propanol, 3-[3-(1-methylcyclohexyl)-4-hydroxy-5-ethylphenyl)propanol, 3-(3-t-butyl-4-hydroxy-5-ethylphenyl)propanol, 3-(3-cyclohexyl-4-hydroxy-5-ethylphenyl)propanol, 3-[3-(1-methylcyclohexyl)-4-hydroxy-5-ethylphenyl)propanol, 3-(3,5-di-t-butyl-2-hydroxyphenyl)propanol, 3-(3,5-di-t-butyl-4-hydroxyphenyl)propanol, 3-(3-t-pentyl-4-hydroxy-5-t-butylphenyl)propanol, 3-(3-t-octyl-4-hydroxy-5-t-butylphenyl)propanol, 3-(3-cyclohexyl-4-hydroxy-5-t-butylphenyl)propanol, 3-[3-(1-methylcyclohexy)-4-hydroxy-5-t-butylphenyl]propanol, 3-(3-t-butyl-2-methoxyphenyl)propanol, 3-(3-t-butyl-4-methoxyphenyl) propanol, 3-(3-t-butyl-5-methoxyphenyl)propanol, 3-(3-t-pentyl-4-methoxyphenyl)propanol, 3-(3-t-octyl-4-methoxyphenyl)propanol, 3-(3-cyclohexyl-4-methoxyphenyl)propanol, 3-[3-(1-methylcyclohexyl)-4-methoxyphenyl)propanol, 3-(3-t-butyl-2-methoxy-5-methylphenyl)propanol, 3-(3-t-butyl-4-methoxy-5-methylphenyl)propanol, 3-(5-t-butyl-2-methoxy-3-methylphenyl)propanol, 3-(3-t-pentyl-4-methoxy-5-methylphenyl)propanol, 3-(3-t-octyl-4-methoxy-5-methylphenyl)propanol, 3-(3-cyclohexyl-4-methoxy-5-methylphenyl)propanol, 3-[3-(1-methylcyclohexy)-4-hydroxy-5-methylphenyl]propanol, 3-(3-t-butyl-4-methoxy-5-ethylphenyl)propanol, 3-(3-t-pentyl-4-methoxy-5-ethylphenyl)propanol, 3-(3-t-octyl-4-methoxy-5-ethylphenyl)propanol, 3-(3-cyclohexyl-4-methoxy-5-ethylphenyl)propanol, 3-[3-(1-methylcyclohexy)-4-hydroxy-5-ethylphenyl]propanol, 3-(3,5-di-t-butyl-2-methoxyphenyl)propanol, 3-(3,5-di-t-butyl-4-methoxyphenyl)propanol, 3-(3-t-pentyl-4-methoxy-5-t-butylphenyl)propanol, 3-(3-t-octyl-4-methoxy-5-t-butylphenyl)propanol, 3-(3-cyclohexyl-4-methoxy-5-t-butylphenyl)propanol, 3-[3-(1-methylcyclohexyl)-4-methoxy-5-t-butylphenyl)propanol, 3-(3-t-butyl-2-ethoxyphenyl)propanol, 3-(3-t-butyl-4-ethoxyphenyl) propanol, 3-(3-t-butyl-4-ethoxy-5-methylphenyl)propanol, 3-(3-t-butyl-2-ethoxy-5-methylphenyl)propanol, 3-(5-t-butyl-2-ethoxy-3-methylphenyl)propanol, 3-(3,5-di-t-butyl-4-ethoxyphenyl)propanol, 3-(3,5-di-t-butyl-2-ethoxypheny) propanol, 4-(3-t-butyl-2-hydroxyphenyl)butanol, 4-(3-t-butyl-4-hydroxyphenyl)butanol, 4-(3-t-butyl-4-hydroxy-5-methylphenyl)butanol, 4-(3-t-butyl-2-hydroxy-5-methylphenyl)butanol, 4-(5-t-butyl-2-hydroxy-3-methylphenyl)butanol, 4-(3,5-di-t-butyl-4-hydroxyphenyl) butanol, 4-(3,5-di-t-butyl-2-hydroxyphenyl)butanol, 4-(3-t-butyl-2-methoxyphenyl)butanol, 4-(3-t-butyl-4-methoxyphenyl)butanol, 4-(3-t-butyl-2-methoxy-5-methylphenyl)butanol, 4-(5-t-butyl-2-methoxy-3-methylphenyl)butanol, 4-(3,5-di-t-butyl-4-methoxyphenyl) butanol, 4-(3,5-di-t-butyl-2-methoxyphenyl)butanol, 5-(3-t-butyl-2-hydroxyphenyl)pentanol, 5-(3-t-butyl-4-hydroxyphenyl)pentanol, 5-(3-t-butyl-4-hydroxy-5-methylphenyl)pentanol, 5-(3-t-butyl-2-hydroxy-5-methylphenyl)pentanol, 5-(5-t-butyl-2-hydroxy-3-methylphenyl)pentanol, 5-(3,5-di-t-butyl-4-hydroxyphenyl) pentanol, 6-(3,5-di-t-butyl-2-hydroxyphenyl)hexanol, 6-(3-t-butyl-2-hydroxyphenyl)hexanol, 6-(3-t-butyl-4-hydroxyphenyl)hexanol, 6-(3-t-butyl-4-hydroxy-5-methylphenyl)hexanol, 6-(3-t-butyl-2-hydroxy-5-methylphenyl)hexanol, 6-(5-t-butyl-2-hydroxy-3-methylphenyl)hexanol, 6-(3,5-di-t-butyl-4-hydroxyphenyl) hexanol and 6-(3,5-di-t-butyl-2-hydroxyphenyl)hexanol.

When A is a *—COR$^7$— group, the hydroxy compound (III) can be produced, for example, by the following known method.

When R$^7$ is a direct bond, it can be produced, for example, by subjecting a corresponding hydroxybenzoic acid, alkoxybenzoic acid, aralkyloxybenzoic acid or the like to the Friedel-Crafts reaction using a catalyst such as aluminum chloride, zinc chloride or the like. When Z is a hydroxyl group, an alkoxy group or an aralkyloxy group, it can be produced, for example, by subjecting a corresponding phenol to the Kolbe-Schmitt reaction using an alkaline metal hydroxide such as sodium hydroxide or potassium hydroxide and carbon dioxide according to the method described in JP-A-62-61949 and 63-165341.

When R$^7$ is alkylene having 1 to 8 carbon atoms, it can be produced, for example, by acylating a corresponding phenol using a Friedel-Crafts catalyst such as aluminum chloride or zinc chloride and carboalkoxyalkanoyl halogenoid according to the method described in Rubber Chemistry and Technology 46, 96 (1973) and then reducing the carbonyl group at the benzyl position to an alkylene group using a hydrolyzing catalyst such as palladium-carbon or platinum-carbon followed by hydrolyzing the ester with an acid or an alkali.

Typical examples of the hydroxy compound (III) when A is a *—COR$^7$— group include 3-t-butyl-2-hydroxybenzoic acid, 3-t-butyl-4-hydroxybenzoic acid, 5-t-butyl-2-hydroxybenzoic acid, 3-t-pentyl-4-hydroxybenzoic acid, 3-t-octyl-4-hydroxybenzoic acid, 3-cyclohexyl-4-hydroxybenzoic acid, 3-(1-methylcyclohexyl)-4-hydroxybenzoic acid, 3-t-butyl-2-hydroxy-5-methylbenzoic acid, 3-t-butyl-4-hydroxy-5-methylbenzoic acid, 5-t-butyl-2-hydroxy-3-methylbenzoic acid, 3-t-pentyl-4-hydroxy-5-methylbenzoic acid, 3-t-octyl-4-hydroxy-5-methylbenzoic acid, 3-cyclohexyl-4-hydroxy-5-methylbenzoic acid, 3-(1-methylcyclohexyl)-4-hydroxy-5-methylbenzoic acid, 3-t-butyl-4-hydroxy-5-ethylbenzoic acid, 3-t-pentyl-4-hydroxy-5-ethylbenzoic acid, 3-t-octyl-4-hydroxy-5-ethylbenzoic acid, 3-cyclohexyl-4-hydroxy-5-ethylbenzoic acid, 3-(1-methylcyclohexyl)-4-hydroxy-5-ethylbenzoic acid, 3,5-di-t- butyl-2-hydroxybenzoic acid, 3,5-di-t-butyl-4-hydroxybenzoic acid, 3-t-pentyl-4-hydroxy-5-t-butylbenzoic acid, 3-t-octyl-4-hydroxy-5-t-butylbenzoic acid, 3-cyclohexyl-4-hydroxy-5-t-butylbenzoic acid, 3-(1-methylcyclohexyl)-4-hydroxy-5-t-butylbenzoic acid, 3-t-butyl-2-methoxybenzoic acid, 3-t-butyl-4-methoxybenzoic acid, 3-t-butyl-5-methoxybenzoic acid, 3-t-pentyl-4-methoxybenzoic acid, 3-t-octyl-4-methoxybenzoic acid, 3-cyclohexyl-4-methoxybenzoic acid, 3-(1-methylcyclohexyl)-4-methoxybenzoic acid, 3-t-butyl-2-methoxy- 5-methylbenzoic acid, 3-t-butyl-4-methoxy-5-methylbenzoic acid, 5-t-butyl-2-methoxy-3-methylbenzoic acid, 3-t-pentyl-4-methoxy-5-methylbenzoic acid, 3-t-octyl-4-methoxy-5-methylbenzoic acid, 3-cyclohexyl-4-methoxy-5-methylbenzoic acid, 3-(1-methylcyclohexyl)-4-methoxy-5-methylbenzoic acid, 3-t-butyl-4-methoxy-5-ethylbenzoic acid, 3-t-pentyl-4-methoxy-5-ethylbenzoic acid, 3-t-octyl-4-methoxy-5-ethylbenzoic acid, 3-cyclohexyl-4-methoxy-5-ethylbenzoic acid, 3-(1-methylcyclohexyl)-4-methoxy-5-ethylbenzoic acid, 3,5di-t-butyl-2-methoxybenzoic acid, 3,5-di-t-butyl-4-methoxybenzoic acid, 3-t-pentyl-4-methoxy-5-t-butylbenzoic acid, 3-t-octyl-4-methoxy-5-t-butylbenzoic acid, 3-cyclohexyl-4-methoxy-5-t-butylbenzoic acid, 3-(3-(1-methylcyclohexyl)-4-methoxy-5-butylbenzoic acid, 3-t-butyl-2-ethoxybenzoic acid, 3-t-butyl-4-ethoxybenzoic acid, 3-t-butyl-4-ethoxy-5-methylbenzoic acid, 3-t-butyl-2-ethoxy-5-methylbenzoic acid, 5-t-butyl-2-ethoxy-3-methylbenzoic acid, 3,5-di-t-butyl-4-ethoxybenzoic acid, 3,5-di-t-butyl-2-ethoxybenzoic acid, (3-t-butyl-2-hydroxyphenyl)acetic acid, (3-t-butyl-4-hydroxyphenyl)acetic acid, (5-t-butyl-2-hydroxyphenyl)acetic acid, (3-t-pentyl-4-hydroxyphenyl)acetic acid, (3-t-octyl-4-hydroxyphenyl)acetic acid, (3-cyclohexyl-4-hydroxyphenyl)acetic acid, [3-(1-methylcyclohexyl)-4-hydroxyphenyl)acetic acid, (3-t-butyl-2-hydroxy-5-methylphenyl)acetic acid, (3-t-butyl-4-hydroxy-5-methylphenyl)acetic acid, (5-t-butyl-2-hydroxy-3-methylphenyl)acetic acid, 3(3-t-pentyl-4-hydroxy-5-methylphenyl)acetic acid, (3-t-octyl-4-hydroxy-5-methylphenyl)acetic acid, (3-cyclohexyl-4-hydroxy-5-methylphenyl)acetic acid, [3-(1-methylcyclohexyl)-4-hydroxy-5-methylphenyl]acetic acid, (3-t-butyl-4-hydroxy-5-ethylphenyl)acetic acid, (3-t-pentyl-4-hydroxy-5-ethylphenyl)acetic acid, (3-t-octyl-4-hydroxy-5-ethylphenyl)acetic acid, (3-t-octyl-4-hydroxy-5-ethylphenyl)acetic acid, (3-cyclohexyl-4-hydroxy-5-ethylphenyl)acetic acid, [3-(1-methylcyclohexyl)-4-hydroxy-5-ethylphenyl]acetic acid, (3,5-di-t-butyl-2-hydroxyphenyl)acetic acid, (3,5-di-t-butyl-4-hydroxyphenyl)acetic acid, (3-t-pentyl-4-hydroxy-5-t-butylphenyl)acetic acid, (3-t-octyl-4-hydroxy-5-t-butylphenyl)acetic acid, (3-cyclohexyl-4-hydroxy-5-t-butylphenyl)acetic acid, [3-(1-methylcyclohexyl)-4-hydroxy-5-t-butylphenyl]acetic acid, (3-t-butyl-2-methoxyphenyl)acetic acid, (3-t-butyl-4-methoxyphenyl) acetic acid, (3-t-butyl-5-methoxyphenyl)acetic acid, (3-t-pentyl-4-methoxyphenyl)acetic acid, (3-t-octyl-4-methoxyphenyl)acetic acid, (3-cyclohexyl-4-methoxyphenyl)acetic acid, [3-(1-methylcyclohexyl)-4-methoxyphenyl]acetic acid, (3-t-butyl-2-methoxy-5-methylphenyl)acetic acid, (3-t-butyl-4-methoxy-5-methylphenyl)acetic acid, (5-t-butyl-2-methoxy-3-methylphenyl)acetic acid, (3-t-pentyl-4-methoxy-5-methylphenyl)acetic acid, (3-t-octyl-4-methoxy-5-methylphenyl)acetic acid, (3-cyclohexyl-4-methoxy-5-methylphenyl)acetic acid, [3-(1-methylcyclohexyl)-4-methoxy-5-methylphenyl]acetic acid, (3-t-butyl-4-methoxy-5-ethylphenyl)acetic acid, (3-t-pentyl-4-methoxy-5-ethylphenyl)acetic acid, (3-t-octyl-4-methoxy-5-ethylphenyl)acetic acid, (3-cyclohexyl-4-methoxy-5-ethylphenyl)acetic acid, [3-(1-methylcyclohexyl)-4-methoxy-5-ethylphenyl]acetic acid, (3,5-di-t-butyl-2-methoxyphenyl)acetic acid, (3,5-di-t-butyl-4-methoxyphenyl)acetic acid, (3-t-pentyl-4-methoxy-5-t-butylphenyl)acetic acid, (3-t-octyl-4-methoxy-5-t-butylphenyl)acetic acid, (3-cyclohexyl-4-methoxy-5-t-butylphenyl)acetic acid, [3-(3-(1-methylcyclohexyl)-4-methoxy-5-butylphenyl]acetic acid, (3-t-butyl-2-ethoxyphenyl)acetic acid, (3-t-butyl-4-ethoxyphenyl)acetic acid, (3-t-butyl-4-ethoxy-5-methylphenyl)acetic acid, (3-t-butyl-2-ethoxy-5-methylphenyl)acetic acid, (5-t-butyl-2-ethoxy-3-methylphenyl)acetic acid, (3,5-di-t-butyl-4-ethoxyphenyl)acetic acid, (3,5-di-t-butyl-2-ethoxyphenyl) acetic acid, 3-(3-t-butyl-2-hydroxyphenyl)propionic acid, 3-(3-t-butyl-4-hydroxyphenyl)propionic acid, 3-(5-t-butyl-2-hydroxyphenyl) propionic acid, 3-(3-t-pentyl-4-hydroxyphenyl)propionic acid, 3-(3-t-octyl-4-hydroxyphenyl)propionic acid, 3-(3-cyclohexyl-4-hydroxyphenyl)propionic acid, 3-[3-(1-methylcyclohexyl)-4-hydroxyphenyl)propionic acid, 3-(3-t- butyl-2-hydroxy-5-methylphenyl)propionic acid, 3-(3-t-butyl-4-hydroxy-5-methylphenyl)propionic acid, 3-(5-t-butyl-2-hydroxy-3-methylphenyl)propionic acid, 3-(3-t-pentyl-4-hydroxy-5-methylphenyl)propionic acid, 3-(3-t-octyl-4-hydroxy-5-methylphenyl)propionic acid, 3-(3-cyclohexyl-4-hydroxy-5-methylphenyl)propionic acid, 3-[3-(1methylcyclohexyl)-4-hydroxy-5-methylphenyl]propionic acid, 3-(3-t-butyl-4-hydroxy-5-ethylphenyl)propionic acid, 3-(3-t-pentyl-4-hydroxy-5-ethylphenyl)propionic acid, 3-t-octyl-4-hydroxy-5-ethylphenyl)propionic acid, 3-(3-cyclohexyl-4-hydroxy-5-ethylphenyl)propionic acid, 3-(3(1-methylcyclohexy)-4-hydroxy-5-methylphenyl)propionic acid, 3-(3,5-di-t-butyl-2-hydroxyphenyl)propionic acid, 3-(3,5-di-t-butyl-4-hydroxyphenyl)propionic acid, 3-(3-t-pentyl-4-hydroxy-5-t-butylphenyl)propionic acid, 3-(3-t-octyl-4-hydroxy-5-butylphenyl)propionic acid, 3-(3-cyclohexyl-4-hydroxy-5-t-butylphenyl)propionic acid, 3-[3(1-methylcyclohexyl-4-hydroxy-5-t-butylphenyl]propionic acid, 3-(3-t-butyl-2-methoxyphenyl)propionic acid, 3-(3-t-butyl-4-methoxphenyl)propionic acid, 3-(3-t-butyl-5-methoxphenyl)propionic acid, 3-(3-t-pentyl-4-methophenyl)propionic acid, 3-(3-t-octyl-4-methophenyl) propionic acid, 3-(3-t-cyclohexyl-4-methoxyphenyl) propionic acid, 3-[3-(1-methylcyclohexyl)-4-methoxyphenyl]propionic acid, 3-(3-t-butyl-2-methoxy-5-methylphenyl)propionic acid, 3-(3-t-butyl-4-methoxy-5-methylphenyl)propionic acid, 3-(5-t-butyl-2-methoxy-3-methylphenyl)propionic acid, 3-(3-t-pentyl-4-methoxy-5-methylphenyl)propionic acid, 3-(3-t-octyl-4-methoxy-5-methylphenyl)propionic acid, 3-(3-t-cyclohexyl-4-methoxy-5-methylphenyl)propionic acid, 3-[3(1-methylcyclohexyl)-4-methoxy-5-methylphenyl]propionic acid, 3-(3-t-butyl-4-methyoxy-5-ethylphenyl)propionic acid, 3-(3-t-pentyl-4-methoxy-5-ethylphenyl)propionic acid, 3-(3-t-octyl-4-methoxy-5-ethylphenyl)propionic acid, 3-(3-t-cyclohexyl-4-methoxy-5-ethylphenyl)propionic acid, 3-[3(1-metyhlcyclohexyl)-4-methoxy-5-ethylphenyl]propionic acid, 3-(3,5-di-t-butyl-2-methoxyphenyl)propionic acid, 3-(3,5-di-t-butyl-4-methoxyphenyl)propionic acid, 3-(3-t-pentyl-4-methoxy-5-t-butylphenyl)propionic acid, 3-(3-t-octyl-4-methoxy-5-t-butylphenyl)propionic acid, 3-(3-cyclohexyl-4-methoxy-5-t-butylphenyl)propionic acid, 3-[3-(3-(1-methylcyclohexyl)-4-methoxy-5-butylphenyl]propionic acid, 3-(3-t-butyl-2-ethoxyphenyl)propionic acid, 3-(3-t-butyl-4-ethoxyphenyl)propionic acid, 3-(3-t-butyl-4-ethoxyphenyl)propionic acid, 3-(3-t-butyl-2-ethoxy-5-methylphenyl)propionic acid, 3-(5-t-butyl-2-ethoxy-3-methylphenyl)propionic acid, 3-(3,5-di-t-butyl-4-ethoxy-5-methylphenyl)propionic acid, 3-(3,5-di-t-butyl-2-ethoxyphenyl)propionic acid, 3-(3-t-butyl-2-hydroxyphenyl)butanoic acid, 3-(3-t-butyl-4-hydroxyphenyl)butanoic acid, 3-(3-t-butyl-4-hydroxy-5-methylphenyl)butanoic acid, 3-(3-t-butyl-2-hydroxy-5-methylphenyl)butanoic acid, 3-(3-t-butyl-2-hydroxy-5-methylphenyl)butanoic acid, 3-(5-t-butyl-2-hydroxy-3-phenyl)butanoic acid, 3-(3,5-di-t-butyl-4-hydroxyphenyl)butanoic acid, 3-(3,5-di-t-butyl-2-hydroxyphenyl)propionic acid, 3-(3-t-butyl-2-methoxyphenyl)butanoic acid, 3-(3-t-butyl-4-methoxyphenyl)butanoic acid, 3-(3-t-butyl-4-methoxy-5-methylphenyl)butanoic acid, 3-(3-t-butyl-2-methoxy-5-methylphenyl)butanoic acid, 3-(5-t-butyl-2-methoxy-3-methylphenyl)butanoic acid, and 3-(3,5-di-t-butyl-2-methoxyphenyl)butanoic acid, Thus, the phosphites (I) of the present invention can be obtained. The hyrolysis resitance of the phosphites (I) of the present invention can be improved by containing amines, acid-bonded metal salts or the like.

Typical examples of the amines include trialkanolamines such as triethanolamine, tripropanolamine and tri-i-propanolamine; dialkanolamines such as diethanolamine, dipropanolamine, di-i-propanolamine, tetraethanolethylenediamine and tetra-i-propanolethylenediamine; monoalkanolamines such as dibutylethanolamine and dibutyl-i-propanolamine; aromatic amines such as 1,3,5-trimethyl-2,4,6-triazine; alkylamines such as dibutylamine, piperidine, 2,2,6,6-tetramethylpiperdine and 4-hydroxy-2,2,6,6-tetramethylpiperdine; polyalkylanapolyamines such as hexamethylenetetramine, triethylenediamine, triethylenetetramine and tetraethylenepantamine; and hindered amine photostabilizers described hereinafter.

Furthermore, there can also be used a long-chain aliphatic amine described in JP-A-61-63686, a compound having a steric hindrance amine group described in JP-A-6-329830, a hindered piperidinyl photostabilizer described in JP-A-7-90270 and an organic amine described in JP-A-7-278164.

A proportion of the amines to be used is normally about 0.01% to 25% by weight based on the phosphites (I).

Typical examples of the acid-bonded metal salt include hydrotalcites. Examples of the hyrotalcites include double salt compounds represented by the following formula:

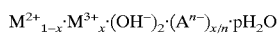

wherein $M^{2+}$ represents Mg, Ca, Sr, Ba, Zn, Pb, Sn or Ni; $M^{3+}$ represents Al, B or Bi; n represents a number of 1 to 4; x represents a number of 0 to 0.5; p represents a number of 0 to 2; and $A^{n-}$ represents an anion having a valence of n).

Specific examples of the anion having a valence of n represented by $A^{n-}$ includes OH—, Cl—, Br—, I—, $ClO_4$—, $HCO_3$—, $C_6H_5COOO$—, $CO_3^{2-}$, $SO^{2-}$, —OOCCOO—, $(CHOHCOO)_2^{2-}$, $C_2H_4(COO)_2^{2-}$, $(CH_2COO)_2^{2-}$, $CH_3CHOHCOO$—, $SiO_3^{2-}$, $SiO_4^{4-}$, $Fe(CN)_6^{4-}$, $BO^{3-}$, $PO_3^{3-}$ and $HPO_4^{2-}$.

Among them, particularly preferred one is, for example, hydrotalcites represented by the following formula:

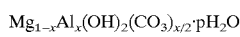

wherein x and p are as defined above.

The hydrotalcites may be natural or systhetic products, and can be used regardless of crystal structure and crystal particle diameter thereof.

Furthermore, an ultra fine zinc oxide described in JP-A-6-329830 and a inorganic compound described in JP-A-7-278164 can also be used.

A proportion of the acid-bonded metal salt to be used is normally about 0.01 to 25% by weight based onthe phosphites (I).

The phosphites (I) of the present invention are effective for stablizing the organic material against heat deterioration and oxidization deterioration. Examples of the organic material which can be stabilized by the phosphites (I) of present invention include (1) polyethylene such as high-density polyethylene (HD-PE), low-density polyethylene (LD-PE) and straight-chain low-density polyethylene (LLDPE)
(2) polypropylene
(3) methylpentene polymer
(4) EEA (ethylene/ethyl acrylate copolymer) resin
(5) ethylene/vinyl acetate copolymer resin
(6) polystrenes such as polystyrene, poly(p-methystyrene) and poly(α-methylstyrene)
(7) As (acrylonitrile/styrene copolymer) resin
(8) ABS (acrylonitrile/butadiene/styrene copolymer) resin
(9) AAS (special acrylic rubber/acrylonitrile/styrene copolymer) resin
(10) ACS (acrylonitrile/chlorinated polyethylene/styrene copolymer) resin
(11) chlorinated polyethylene, polychloroprene, chlorinated rubber
(12) polyvinyl chloride, polyvinylidene chloride
(13) methacrylic resin
(14) etyhylene/vinyl alcohol copolymer resin
(15) fluororesin
(16) polyacetal
(17) grafted polyphenylene ether resin and polyphenylene sulfide resin
(18) polyurethane
(19) polyamide
(20) polyester resin such as polyethylene terephthalate and polybutylene terephthalate
(21) polycarbonate
(22) polyacrylate
(23) polysulfone, polyether ether ketone, polyether sulfone
(24) thermoplastic resin such as aromatic polyester resin,
(25) epoxy resin
(26) diallyl phthalate prepolymer
(27) silicone resin
(28) unsaturated polyester resin
(29) acrylic-modified benzoguanamine resin
(30) benzoguanamine/melamine resin
(31) thermosetting resin such as urea resin
(32) polybutadiene
(33) 1,2-polybutadiene
(34) polyisoprene
(35) styrene/butadiene copolymer
(36) butadiene/acrylonitrile copolymer
(37) ethylene/propylene copolymer
(38) silicone rubber
(39) epichlorohydrin rubber
(40) acrylic rubber
(41) natural rubber
(42) chlorinated rubber paint
(43) polyester resin paint
(44) urethane resin paint
(45) epoxy resin paint
(46) acrylic resin paint
(47) vinyl resin paint
(48) aminoalkyd resin paint

(49) alkyd resin
(50) nitrocellulose resin paint
(51) oil-based paint
(52) wax, and
(53) lubricating oil.

Organic materials, such as those exemplified above, can be stabilized alone or in combination thereof by the phosphite (I) of the present invention. Organic materials which can be stabilized by the phosphite (I) of the present invention are not limited to those exemplified above.

The phosphite (I) of the present invention is particularly preferably used for stabilizing the thermoplastic resin, such as polyethylene (e.g. HD-PE, lD-PE and LIDPE), other polyolefins (e.g. polypropylene), and engineering resins such as polyamide, polyethylene terephthalate, polybutylene terephthalate and polycarbonare, among the organic materials exemplified above.

The polyolefins which can be stabilized by the phosphite (I) of the present invention are not specifically limited. For example, they may be obtained by a radical polymerization or may be produced by a polymerization using a catalyst containing a metal of Group IVb, Vb, VIb or VIII of the periodic table. The cataylst containg such a metal may be metal complex which is coordinated by one nor more ligands, for example, oxide which is coordinated by a π or σ bond, halogenated compound, alcolate, ester, aryl and the like, and these complexes may be used as it is, or as a supported cataylst on a carrier such as magnesium chlorid, titanium chlorid, alumina, or silicon oxide.

Among the polyolefin, those produced by using Zielger-Natta cataysr, TNZ catalyst, metallacen catalyst, Phillips catalyst and the like are more suitable for being stabilized by the phosphite (I) of the present invention.

The engineering resins which can be stabilized by the phosphite (I) of the present invention is not specifically limited, either. Polyamide resins which have an amide bond at the polymer chain and can be molten with heating can be stabilized by the phosphite (I) of the present invention. Example of the poriamide resins includethose produced by any mehtod such as condensation reaction between diamines and dicarboxylic acids, condensation reaction of aminocarboxylic acids and ring opening polymerization of lactams. Typical examples thereof includ nylon 66, nylon 69, nylong 610, nylong 612, poly-bis(p-aminocyclohexyl) methanedodecamide, nylon 46, nylon 12, nylon 66/6 which is a coopolymer of nylon 66 and nylon 6, and other copolymer such as nylon 6/12.

Polyester resins which have an ester bond at the polymer chain and can be molten with heating can be stabilized by the phosphite (I) of the present invention. Examples thereof include polyester obtained by the polycondensation between dicarboxylic acids and a dihydroxy compound. The polyester may be a homopolyester of a copolyester.

Polycarbonates which have a carbonate bond at the polymer chain and can be molten with heating can be stabilized by the phosphite (I) of the present invention. Examples thereof include polycarbonate obtained by reacting an aromatic hydroxy compound, or an aromatic hydroxy compound and a small amount of polyhydroxy compound, with a carbonat precursor such as phosgene or diphenyl carbonate in the presence of a solvent, an acid receptor and a molecular weight modifier. The polycarbonate resin may be straight-chain or branched resin, or may be copolymer.

When the organic material is stabilized by the phosphites (I) of the present invention, the phosphites (I) are normally formulated in an amount of about 0.01 to 5 parts by weight, preferably about 0.03 to 3 parts by weight, more preferably about 0.05 to 1 parts by weight, based on 100 parts by weight of the organic material. When the amount is less the 0.01 parts by weight, the stabilizing effect is not sufficient, necessarily. On the other hand, even when the amount exceeds 5 parts by weight, the improvement of the effect corresponding to the amount is not obtained and it is economically disadvantages.

When the phosphites (I) of the present invention are contained in the organic material, if necessary, there can also be contained other additives such as phenol antioxidant, sulfur antioxidant, phosphorous antioxidant, ultraviolet absorber, photostabilizer, peroxide scavenger, polyamide stabilizer, hydroxylamine, lubricant, plasticizer, flame retardant, nucleating agent, metal inactivating agent, anti-static agent, pigment, filler, anti-blocking agent, surfactant, processing aid, foaming agent, emulsifier, brightener, calcium stearate, neutralizing agent (e.g. hydrotalcite), coloring modifier (e.g. 9,10-dihydro-9-oxa-10-phosphophenanthrene-10oxide) and auxiliary stabilizer (e.g. benzofurans or indolines described in U.S. Pat. Nos. 4,325,853, 4,338,244, 5,175,312, 5,216,053, 5,252,643 or 4,316,611, DE-A-4,316,622 or 4,316,876, or EP-A-589,839 or 591,102). These additives can be formulated together with the phosphites (I), and also be formulated in the stage other than the stage where the phosphites (I) are formulated.

Examples of the phenol antioxidant include the following:

(1) Examples of alkylated monophenol 2,6-di-t-butyl-4-methyphenol, 2,4,6-tri-t-butylphenol, 2,6-di-t-butyl-4-butylphenol, 2-t-butyl-4,6-dimethyphenol, 2,6-di-t-butyl-4-ethyphenol, 2,6-di-t-butyl-4-n-butylphenol, 2,6-di-t-butyl-4-isobutylphenol, 2,6-dicyclopentyl-4-methyphenol, 2(α-methylcyclohexy)-4,6-dimethyphenol, 2,6-dioctadecyl-4-methyphenol, 2,4,6-tricyclohexylphenol, 2,6-di-t-butyl-4-methoxymethylphenol, 2,6-di-nonyl-4-methyphenol, 2,4-dimethyl-6-(1'-methylundecyl-1'-yl) phenol, 2,4-dimethyl-6'-(1'-methylheptadecyl-1'-yl)phenol, 2,4-dimethyl-6-(1'-methyltridecyl-1'-yl)phenol and a mixture thereof.

(2) Examples of alkylthiomethylphenol 2,4-dioctylthiomethyl-6-t-butylphenol, 2,4-dioctylthiomethyl-6-methylphenol, 2,4-dioctylthiomethyl-6-ethylphenol, 2,6-didodecylthiomethyl-4-nonylphenol and a mixture thereof (3) Examples of hydroquinone and alkylated hydroquinone 2,6-di-t-butyl-4-methoxyphenol, 2,5-di-t-butylhydroquinone, 2,5-di-t-amylhydroquinone, 2,6-diphenyl-4-octadecyloxyphenol, 2,6-di-t-butylhydroquinone, 2,5-di-t-butyl-4-hydroxyanisole, 3,5-di-t-butyl-4-hydroxyphenyl stearate, bis(3,5-di-t-butyl-4-hydroxyphenyl)adipate and a miture thereof (4) Examples of tocopherol α-tocopherol, β-tocopherol, γ-tocopherol, δ-tocopherol, and a mixture thereof (5) Examples of hydroxylated thiodiphenyl ether 2,2'-thiobis(6-t-butylphenol), 2,2'-thiobis(4-methyl-6-t-butylphenol), 2,2'-thiobis(4-octylphenol), 4,4'-thiobis(3-methyl-6-t-butylphenol), 4,4'-thiobis(2-methyl-6-t-butylphenol), 4,4'-thiobis(3,6-di-t-amylphenol), 4,4'-(2,6-dimethyl-4-hydroxyphenyl)disulfide and the like (6) Examples of alkylidenebisphenol and derivation thereof 2,2'-methylenebis(4-methyl-6-t-butylphenol), 2,2'-methylenebis(4-ethyl-6-t-butylphenol), 2,2'-methylenebis[4-methyl-6-(α-methylcyclohexyl)phenol)], 2,2'-methylenebis(4-methyl-6-cyclohexyphenol), 2,2'-methylenebis(4-methyl-6-nonphenol), 2,2'-methylenebis(4, 6-di-t-butylphenol), 2,2'-ethylidenebis(4,6-di-t-butylphenol), 2,2'-ethylidenebis(4-isobutyl-6-t-butylphenol), 2,2'-methylenebis[6(α-methylbenzyl)-4-nonylphenol],2,2'-methylenebis[6-(α,α-dimethylbenzyl)-4-nonylphenol), 4,4'-methylenebis(6-t-butyl-2-methylphenol), 4,4'-methylenebis(2,6-di-t-butylphenol), 4,4'-butylidenebis(3-methyl-6-t-butylphenol), 1,1-bis(4-hydroxyphenyl)cyclohexane, 1,1-bis-(4-hydroxyphenyl)cyclohexane, 1,1-bis(5-t-butyl-4-hydroxy-2-methylphenyl)butane, 2,6-bis[3-t-butyl-5-methyl-2-hydroxybenzyl)-4-methylphenol, 1,1,3-tris(5-t-butyl-4-hydroxy-2-methylphenyl)butane, 1,1-bis(5-t-butyl-4-hydroxy-2-methylphenyl)-3-n-dodecylmercaptobutane, bis[3,3-bis-3'-t-butyl-4'-hydroxyphenyl)butyrate], bis(3-t-butyl-4-hydroxy-5-methylphenyl)dicyclopentadiene, bis[2-(3'-t-butyl-2'-hydroxy-5'-methylbenzyl)-6-t-butyl-4-methylphenyl] terephthalate, 1,1-bis(3,5-dimethyl-2-hydroxyphenyl)butane, 2,2-bis(3,5-di-t-butyl-4-hydroyphenyl)propane, 2,2-bis(5-t-butyl-4-hydroxy-2-methylphenyl)-4-n-dodecylmercaptobutane, 1,1,5,5-tetra(5-t-butyl-4-hydroxy-2-methylphenyl)pentane, 2-t-butyl-6-(3'-t-butyl-5'-methyl-2'-hydroxybenzyl)-4-methylphenyl acrylate, 2,4-di-t-pentyl-6-[1-(2-hydroxy-3,5-di-t-pentylphenyl)ethyl]phenyl acrylate and a mixture thereof.

(7) Examples of O-, N- and S-benzyl derivative 3,5,3',5'-tetra-t-butyl-4,4'-dihydroxydibenzylether, octadodecyl-4-hydroxy-3,5-dimethylbenzylmercapto acetate, tris(3,5-di-t-butyl-4-hydroxybenzyl)amine, bis(4-t-butyl-3-hydroxy-2,6-dimethylbenzyl)dithioterephthalate, bis(3,5)-di-t-butyl-4-hydroxybenzyl)sulfide, isooctyl-3,5-di-t-butyl-4-hydroxybenzylmercapto acetate and a mixture thereof (8) Examples of hydroxybenzylated malonate derivative dicctadecyl-2,2-bis(3,5-di-t-butyl-2-hydroxybenzyl)malonate, dioctadecyl-2-(3-t-butyl-4-hydroxy-5-methylbenzyl)malonate, didodecylmercaptoethyl-2,2-bis(3,5-di-t-butyl-4-hydroxybenzyl)malonate, bis[4-(1,1,3,3-tetramethylbutyl)phenyl]-2,2-bis(3,5-di-t-butyl-4-hydroxybenzyl)malonate and a mixture thereof (9) Examples of aromatic hydroxybenzyl derivative 1,3,5-trimethyl-2,4,6-tris(3,5-di-t-butyl-4-hydroxybenzyl)benzene, 1,4-bis(3,5-di-t-butyl-4-hydroxybenzyl)-2,3,5,6-tetramethylbenzene, 2,4,6-tris(3,5-t-butyl-4-hydroxybenzyl)phenol and a mixture thereof

(10) Examples of triazine derivative 2,4-bis(n-octylthio)-6-(4-hydroxy-3,5-di-t-butylanilino)-1,3,5-triazine, 2-n-ocytlthio-4,6-bis(4-hydroxy-3,5-di-t-butylanilino)-1,3,5-triazine, 2-n-octylthio-4,6-bis(4-hydroxy-3,5-di-t-butylphenoxy)-1,3,5-triazine, 2,4,6-tris(3,5-di-t-butyl-4-hydroxy)-1,3,5-triazine, tris(4-t-butyl-3-hydroxy-2,6-dimethylbenzyl isocyanurate, tris(3,5-di-t-butyl-4-hydroxybenzyl)isocyanurate, 2,4,6-tris(3,5-di-t-butyl-4-hydroxyphenylethyl)-1,3,5-triazine, 2,4,6-tris(3,5-di-t-butyl-4-hydroxyphenylpropyl)-1,3,5-triazine, tris(3,5-dicyclohexyl-4-hydroxybenzyl)isocyanurate, tris[2-(3',5'-di-t-butyl-4'-hydroxycinnamoyloxy)ethyl]isocyanurate and a mixture thereof

(11) Examples of benzyl phosphonate derivative dimethyl-3,5-di-t-butyl-4-hydroxybenzyl phosphonate, diethyl-3,5-di-t-butyl-4-hydroxybenzyl phosphonate, dioctadecyl-3,5-di-t-butyl-4-hydroxybenzyl phosphonate, dioctadecyl-5-t-butyl-4-hydroxy-3-methylbenzyl phosphonate, calcium salt of 3,5-di-t-butyl-4-hydroxybenzyl phosphonic acid monoester and a mixture thereof

(12) Examples of acylaminophenol derivative anilide 4-hydroxylaurate, anilide 4-hydroxystearate, octyl-N-(3,5-di-t-butyl-4-hydroxyphenyl)carbanate and a mixture thereof

(13) Est of β-(3,5-di-t-butyl-4-hydroxyphenyl)propionic acide and the following monohydric or polyhydric alcohol:

methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanuarte, N,N'-bis(hydroxyethyl)oxamide, 3-thiaundecanol, 3-thiapentadecanol, triemthylhexanediol, trimethylolpropane, 4-hydroxymethyl-1-phospha-2,6,7-trioxabicyclo[2,2,2,]octane and a mixture thereof

(14) Ester of β-(5-t-butyl-4-hydroxy-3-methyphenyl)propionic acid and the following monohyric or polyhydric alcohol:

methanol, ethanol, octanol, octadecanol, ethylene glycol, 1,3-propanediol, 1,4-butanediol, 1,6-hexanediol, 1,9-nonanediol, neopantyl glycol, diethylene glycol, thioethylen glycol, spiro glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof

(15) Ester of β-(3,5-dicyclohexyl-4-hydroxyphenyl) propionic acid and the following monohydric or polyhydric alcohol:

methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2,]octane and a mixture thereof

(16) Ester of 3,5-di-t-butyl-4-hydroxyphenylacetic acid and the following monohydric or polyhydric alcohol:

methanol, ethanol, octanol, octadecanol, ethylene glycol, 1,3-propanediol, 1,4-butanediol, 1,6-hexanediol, 1,9-nonanediol, neopentyl glycol, diethylene glycol, thioethylene glycol, spiro glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2,2,2]octane and a mixture thereof

(17) Amide of β-(3,5-di-t-butyl-4-hydroxyphenyl) propionic acid and the following amine:

N,N'-bis(3',5'-di-t-butyl-4'-hydroxyphenyl)propionyl] hydrazine, N,N'-bis[3-(3',5'-di-t-butyl-4'-hydroxyphenyl)propionyl]hexamethylenediamine, N,N'-bis[3-(3',5'-di-t-butyl-4'-hydroxyphenyl)propionyl]

Examples of the sulfur antioxidant include:

dilauryl 3,3'-thiodipropionate, tridecyl 3,3'-thiodipropionate, dimyristyl 3,3'-thiodipropionate, distearyl 3,3'-thiodipropionate, lauryl stearyl 3,3'-thiodipropionate, neopentanetetraylkis(3-lauryl thiopropinate) and a mixture thereof.

Examples of the phosphorous antioxidant include:

triphenyl phosphite, tris(nonylphenyl)phosphite, tris(2,4-di-t-butylphenyl)phosphite, trilauryl phosphite, trioctadecyl phosphite, distearyl pentaerythritol diphosphite, diisodecyl pentaerythritol diphosphite, bis(2,4-di-t-butylphenyl)pentaerythritol diphosphite, bis(2,4-di-t-butyl-6-methylphenyl)pentaerythritol diphosphite, bis(2,4-di-t-butyl-6-methylphenyl)pentaerythritol diphosphite, bis(2,6-di-t-butyl-4-methylphenyl)pentaerythritol diphosphite, bis (2,4,6-tri-t-butylphenyl)pentaerythritol diphosphate, tristearyl sorbitol triphosphite, tetrakis(2,4-di-t-butylphenyl) -4,4'-diphenylene diphosphite, 2,2'-methylenebis(4,6-di-t-butylphenyl)2-ethylhexyl phosphite, 2,2'-ethylidenebis(4,6-di-t-butylphenyl)fluoro phosphite, bis(2,4-di-t-butyl-6-methylphenyl)ethyl phosphite, bis(2,4-di-t-butyl-6-methylphenyl)methyl phosphite, (2,4,6-tri-t-butylphenyl)-5-ethyl-5-butyl-1,3,2-oxaphosphorinane, 2,2',2"-nitrilo [triethyl-tris(3,3',5,5'-tetra-t-butyl-1,1'-biphenyl-2,2'-diyl) phosphite and a mixture thereof.

Examples of the ultraviolet absorber include the followings.

(1) Example of salicylate derivative phenyl salicylate, 4-t-butylphenyl salicylate, 2,4-di-t-butylphenyl3',5'-di-t-butyl4'-hydroxybenzoate, 4-t-octylphenyl salicylate, bis(4-t-butylbenzoyl)resorcinol, benzoylresorcinol, hexadecyl 3',5'-di-t-butyl-4'-hydroxybenzoate, octadecyl 3',5'-di-t-butyl-4'-hydroxybenzoate, 2-methyl4,6-di-t-butylphenyl 3',5'-di-t-butyl-4'-hydroxybenzoate and a mixture thereof.

(2) Examples of 2-hydroxybenzophenone derivative 2,4-dihydroxybenzophenone, 2-hydroxy-4-methoxybenzophenone, 2-hydroxy-4-octoxybenzophenone, 2,2'-dihydroxy-4-methoxybenzophenone, bis(5-benxoyl-4-hydroxy-2-methoxyphenyl)methane, 2,2',4,4'-tetrahydroxybenzophenone and a mixture thereof.

(3) Examples of 2-(2'-hydroxyphenyl)benzotriazole 2-(2-hydroxy-5-methylphenyl)benzotriazole, 2-(3',5'-di-t-butyl-2'-hydroxyphenyl)benzotriazole, 2-(5'-t-butyl-2'-hydroxyphenyl)benzotriazole, 2-(2'-hydroxy-5'-t-octylphenyl)benzotriazole, 2-(3-t-butyl-2-hydroxy-5-methylphenyl)-5-chlorobenzotriazole, 2-(3'-s-butyl-2'-hydroxy-5'-t-butylphenyl)benzotriazole, 2-(2'-hydroxy-4'-octyloxphenyl)benzotriazole, 2-(3',5'-di-t-amyl-2'-hydroxyphenyl)benzotriazole, 2-[2'-hydroxy-3',5'-bis (α,α-dimethylbenzyl)phenyl]-2H-benzotriazole, 2-[(3'-t-butyl-2'-hydroxyphenyl)-5'-(2-octyloxycarbonylethyl)phenyl]-5-chlorobenzotriazole, 2-[3'-t-butyl5'-[2-(2-ethylhexyloxy) carbonlethyl]-2'-hydroxyphenyl]-5-chlorobenzotriazole, 2-[3'-t-butyl-2'-hydroxy-5'-(2-methoxycarbonlethyl)phenyl] -5-chlorobenzotriazole, 2-[3'-t-butyl-2'-hydroxy-5'-(2-methoxycarbonlethyl)phenyl]benzotriazole, 2-[3'-t-butyl-2'-hydroxy-5-(2-octyloxycarbonylethyl)phenyl]benzotriazole, 2-[3'-t-butyl-2'-hydroxy-5'-[2- (2-ethylhexloxy) carbonylethyl]phenyl]benzotriazole, 2-[2-hydroxy-3-(3,4,5, 6-tetrahydrophthalimidemethyl)-5-methylphenyl] benzotriazole, 2(3',5'-di-t-butyl-2-hydroxyphenyl)-5-chlorobenzotriazole, mixture of 2-(3'-dodecyl2'-hydroxy-5'-methylphenyl)benzotriazole and 2-[3'-t-butyl-2'-hydroxy5'-(2-isooctyloxycarbonylethyl)phenyl]benzotriazole, 2,2'-methylenebis]6-(2H-benzotriazol-2-yl)-4-(1,1,3,3-tetramethylbutyl)phenol, 2,2'-memthylenebis[4-t-butyl-6-(2H-benzotriazol-2-yl)phenol], condensate of poly(3-11) (ethylene glycol) and 2-[3'-t-butyl-2'-hydroxy-5'-(2-methoxycarbonylethyl)phenyl]benzotriazole, condensate of poly (3-11) (ethylene glycol) and methyl 3-[3-(2H-benzotriazol-2-yl)-5-t-butyl-4-hydroxyphenyl]propionate, 2-ethylhexyl 3-[3-t-butyl-5-(5-chloro-2H-benzotriazol-2-yl) -4-hydroxyphenyl]propionate, octyl 3-[3-t-butyl-5-(5-chloro-2H-benzotriazol-2-yl)-4-hydroxyphenyl]propionate, methyl 3-[3-t-butyl-5-(5-chloro-2H-benzotriazol-2yl)-4-hydroxyphenyl]propionate, 3-[3-t-butyl-5-(5-chloro-2H-benzotriazol-2yl)-4-hydroxyphenyl]propionic acide and a mixture thereof.

Examples of the photo stabilizer include the followings.

(1) Examples of hindered amine photo stabilizer bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(N-octoxy-2,2,6,6-tetramethyl-4-piperidyl)sebacate, bis(N-benzyloxy-2,2,6,6-tetramethyl-4-piperidyl)sebacate, bis(N-cyclohexyloxy-2,2, 6,6-tetramethyl-4-piperidyl)sebacate, bis(1,2,2,6,6-pantamethyl-4-piperidyl) 2-(3,5-di-t-butyl-4-hydroxybenzyl)-2-butylmalonate, bis(1-acrolyl-2,2,6,6-tetramethyl-4-piperidyl) 2,2-bis(3,5-di-t-butyl-4-hydroxybenzyl)-2-butylmalonate, bis(1,2,2,6,6-penatmethyl-4-piperidyl decanedioate, 2,2,6,6-tetramethyl-4-piperidyl methacrylate, 4 [3-(3,5-di-t-butyl-4-hydroxyphenyl)propionyloxy]-1-[2-(3-(3,5-di-t-butyl-4-hydroxyphenyl)propionyloxy ethyl]-2,2,6,6-tetramethylpiperidine, 2-methyl-2-(2,2,6,6-tetramethyl-4-piperidyl)amino-N-(2,2,6,6-tetramethyl-4-piperidyl) propionamide, tetarkis (2,2,6,6-tetramethyl-4-piperidyl) 1,2, 3,4-butaneteracarboxylate, tetrakis(1,2,2,6,6-pentamethyl-4-piperidyl) 1,2,3,4-butanetetracarboxylate, mixed esterified product of 1,2,3,4-butanetetracarboxylic acid and 1,2,2,6,6-pentamethyl-4-piperidinol and 1-tridecanol, mixed esterified product of 1,2,3,4-butanetetracarboxylic acid and 2,2,6,6-tetramethyl-4-piperidinol and 1-tridecanol, mixed esterified product of 1,2,3,4-butanetetracarbxylic acid and 1,2,2,6,6-pentamethyl-4-piperidinol and 3,9-bis(2-hydroxy-1,1-dimethylethyl)-2,4,8,10-tetraoxaspiro[5.5]undecane, mixed esterified product of 1,2,3,4-butanetetracarboxylic acid and 2,2,6,6-tetarmethyl-4-piperidinol and 3,9-bis(2-hydroxy-1, 1-dimethyethyl)-2,4,8,10-tetraoxaspiro[5.5]undecane, polycondensate of dimethyl succinate and 1-(2-hydroxyethyl)4-hydroxy-2,2,6,6-tetramethylpiperidine, poly[(6-morpholino-1,3,5-triazin-2,4-diyl)((2,2,6,6-tetramethyl-4-piperidyl)imino)hexamethylene ((2,2,6,6-tetramethyl-4-piperidyl)imino)], poly[(60(1,1,3,3-tetramethylbutyl)imino-1,3,5-triazin-2,4-diyl ((2,2,6,6-tetramethyl4-piperidyl) imino)hexanmethylene ((2,2,6,6-tetremethyl-4-piperidyl) imino)], polycondensate of N,N'-bis(2,2,6,6-tetramethyl-4-piperidyl)hexamethylenediamine and 1,2-bromoethane, N,N',4,7-tetrakis[4,6-bis(N-butyl-N-(2,2,6,6-tetramethyl-4-piperidyl)amino)-1,3,5-triazin-2-yl]-4,7-diazadecane-1,10 diamine, N,N',4-tris[4,6-bis(N-butyl-N-(2,2,6,6-tetramethyl-4-piperidyl)amino)-1,3,5-triazin-2-yl ]-4,7-diazadecane-1,10 diamine, N,N', 4,7-tetrakis[4,6-bis(N-butyl-N-(1,2,2,6,6-pentamethyl-4-piperidyl)amino)-1,3,5-triazin-2-yl]-4,7-diazadecane-1,10 diamine, N,N',4-tris[4,6-bis(N-butyl-N-(1,2,2,6,6-pentamethyl-4-piperidyl)amino)-1,3,5-triazin-2-yl]-4,7-diazadecane-1,10 diamine and a mixture thereof.

(2) Examples of acrylate photo stabilizer ethyl α-cyano-β, β-dipheylacrylate, isooctyl α-cyano-β, β-diphenylacrylate, methyl α-carbonmethoxycinnamate, methyl α-cyano-β-methyl-methyoxycinnamate, butyl α-cyano-β-methyl-p-methoxycinnamate, N-(β-carbonmethoxy-β-cyanovinyl)-2-methylindoline and a mixture thereof.

(3) Examples of nickel photo stabilizer nickel complex of 2,2'-thiobis-[4-(1,1,3,3-tetremethylbutyl)phenol], nickel dibutyldithiocarbamate, nickel salt of monoalkyl ester, nickel complex of ketoxime and a mixture thereof.

(4) Examples of oxamide photo stabilizer 4,4'-dioctyloxyoxanilide, 2,2'-diethoxyoxanilide, 2,2'-dioctyloxy-5,5'-di-t-butylanilide, 2,2'-didodecyloxy-5,5'-di-t-butylanilide, 2-ethoxy-2'-ethyloxanilide, N,N'-bis(3- dimethylaminopropyl)oxamide, 2-ethoxy-5-t-butyl-2'-ethoxyanilide, 2-ethoxy-5,4'-di-t-butyl-2'-ethyloxanilide and a mixture thereof.

(5) Examples of 2-(2-hydroxyphenyl)-1,3,5-triazine photo stabilizer 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2,-(2-hydroxy-4-octyloxyphenyl)-4,6-(4-methylphenyl)-1,3,5-triazine, 2,(2-hydroxy-4-dodecyloxyphenyl)-4,6-bis(4-methylphenyl)-1,3,5-triazine, 2-[2-hydroxy-4-(2-hydroxy-3-butyloxypropoxy)phenyl]-4,6-bis(2,4-dimethylphenyl)-1,3,5-triazine, 2-[2-hydroxy-4-(2-hydroxy-3-octyloxypropoxy)phenyl]-4,6-bis(2,4-dimethylphenyl)-1,3,5-triazine and a mixture thereof.

Examples of the metal inactivating agent include: N,N'-diphenyloxamide, N-salicylal-N'-salicyloylhydrazine, N,N'-bis(salicyloyl)hydrazine, N,N'-bis(3,5-di-t-butyl-4-hydroxyphenylpropionyl)hydrazine, 3-salicyloylamino-1,2,4-triazole, bis(benzylidene)oxalyl dihydrazide, oxalinide, isophthaloyl dihydrazide, sebacoylbisphenyl hydrazie, N,N'-bis(salicyloyl)thiopropionyl dihydrazide and a mixture thereof.

Examples of the peroxide scavenger include ester of β-thiodipropionic acid, mercaptobenzoimidazole, zinc salt of 2-mercaptobenzoimidazole, zinc sald of dibutyldithiocarbamic acid, dioctadecyl disulfide, pentaerythritol tetrakis(β-dodecylmercapto)propionate and a mixture thereof.

Examples of the polyamide stabilizer include copper of divalent manganese salts of iodide or phosphorous compound and a mixture thereof.

Examples of the hydroxyamine include N,N'-dibenzylhydroxyamine, N,N-diethylhydroxyamine, N,N-dioctylhydroxyamine, N,N-dilaurylhydroxyamine, N,N-detetradecylhydroxyamine, N,N-dihexadecylhydroxyamine, N,N-dioctadecylhydroxyamine, N,N-dibenzylhydroxyamine, N,N-dibenzylhydroxyamine, N-heptadecyl-N-octadecylhydroxyamine and a mixture thereof.

Examples of the neutralizing agent include calcium stearate, zinc stearate, magnesium stearate, hydrotalcite such as alkali magnesium aluminum hydroxy carbonate hydride, melamine, amine, polyamide, polyurethane and a mixture thereof.

Examples of the lubricant includ aliphatic hydrocarbon such as paraffin or was, higher aliphatic acid having 8 to 22 carbon atoms, higher aliphatic acide (having 8 to 22 carbon atoms)metal (Al, Ca, Mg, Zn) salt, aliphatic alcohol having 8 to 22 atoms, polyglycol, ester of higher fatty acid having 4 to 22 carbon atoms and aliphatic monohydric alcohol having 4 to 18 carbon atoms, higher aliphatic amide having 8 to 22 carbon atoms, silicone oil, rosin derivative and the like.

Examples of the nucleating agent include the followings. sodium 2,2'-methylenebis(4,6-di-t-butylphenyl) phosphate, [phosphoric acid-2,2'-methylenebis(4,6-di-t-butylphenyl)] dihydroxyaluminum, bis[phosphoric acid-2,2'-methylenebis(4,6-di-t-butylphenyl)]dihydroxyaluminum, tris[phosphoric acid-2,2'-methylenebis(4,6-di-t-butylphenyl)]aluminum, sodium bis(4,6-di-t-butylphenyl) phosphate, benzoic acid metal salt such as sodium benzoate, aluminum p-t-butylbenzoate, 1,3:2,4-bis(O-benzylidene)sorbitol, 1,3:2,4-bis (O-ethylbenzylidene)sorbitol, 1,3-O-3,4-dimethylbenzylidene-2,4-O-benzylidenesorbitol, 1,3-O-benzylidene-2,4-0-3,4-dimethylbenzylidene sorbitol, 1,3:2,4-bis(O-3,4-dimethylbenzylidene)sorbitol, 1,3-O-p-chlorobenzylidene-2,4-O-3,4-dimethylbenzylidene sorbitol, 1,3-O-3,4-dimethylbenzylidene-2,4-O-p-chlorobenzylidene sorbitol, 1,3:2,4-bis(O-p-chlorobenzylidene)sorbitol and a mixture thereof.

Examples of the filler includ calcium carbonate, silicate, glass fiber, asbestos, talc, kaoline, mica barium sulfate, carbon black, carbon fiber, zeolite and a mixture thereof.

Among these additives, those which are preferably used include phenol antioxidant, phosphorous antioxidant, ultraviolet absorber, hindered amine photo stabilizer, peroxide scavenger and neutralizing agent.

Examples of the preferred phenol antioxidant include the following compounds, and a mixture of two or more knds of them can also be used:

2,6-di-t-butyl-4-methylphenol, 2,4,6-tri-t-butylphenol, 2,4-dioctylthiomethyl-ϵ-methylphenol, 2,2'-thiobis(6-t-butylphenol), 4,4'-thiobis(3-methyl-6-t-butylphenol), 2,2'-methylenebis(4-methyl-6-t-butylphenol), 2,2'-methylenebis[4-ethyl-6-t-butylphenol], 2,2'-methylenebis(4-ethyl-6-(α-methylcyclohexyl)phenol], 2,2'-methylenebis(4-methyl-6-cyclohexylphenol), 2,2'-methylenebis(4,6-di-t-butylphenol), 2,2'-ethylidenebis(4,6-di-t-butylphenol), 4,4'-methylenebis(6-t-butyl-2-methyphenol), 4,4'-methylenebis(2,6-di-t-butylphenol), 4,4'-mbutylidenebis(3-methyl-6-t-butylphenol), 1,1'-bis(4-hydroxyphenyl)cyclohexane, 1,1-bis(5-t-butyl-4-hydroxy-2-methylphenyl)butane, 1,1,3-tris(5-t-butyl-4-hydroxy-2-methylphenyl)butane, ethylene glycol, bis [3,3-bis-3'-t-butyl-4'-hydroxyphenyl)butyrate], 2-t-butyl-6-(3'-t-butyl-5'-methyl2'-hydroxybenzyl)-4-methylphenyl acrylate, 2,4-fi-t-pentyl-6-[1-(2-hydroxy-3,5-di-t-pentylphenyl)ethyl]phenyl acrylate, 2,4,6-tris(3,5-di-t-butyl-4-phneoxy)-1,3,5-triazine, tris(4-t-butyl-3-hydroxy-2,6-dimethylbenzyl)isocyanurate, tris(3,5-di-t-butyl-4-hydroxybenzyl)isocyanurate, tris[2- (3',5'-di-t-butyl-4'-hydroxycinnamoyloxy)ethyl)isocyanurate, diethyl-3,5-di-t-butyl-4-hydroxybenzyl phosphate, di-n-octadecyl-3,5-di-t-butyl-4-hydroxybenzyl phosphonate, calcium salt of 3,5-di-t-butyl-4-hydroxybenzylphosphonic acid monoester, n-octadecyl 3-(3,5-di-t-butyl-4-hydroxyphenyl)propionate, neopentanetetrayltetrakis(3,5-di-t-butyl-4-hydroxycinnamate), thiodiethylenebis(3,5-di-t-butyl-4-hydroxycinnamate), 1,3,5-trimethyl-2,4,6-tris(3,5-di-t-butyl-4-hydroxybenzyl)benzene, 3,6-dioxaoctamethylenebis(3,5-di-t-butyl-4-hydroxycinnamate), hexamethylenebis(3,5-di-t-butyl-4-hydroxycinnamate), triethylene glycol bis(5-t-butyll-4-hydroxy-3-methylcinnamate), 3,9-bis[2-(3-(3-t-butyl-4-hydroxy-5-methylphenyl)propionyloxy)-1,1-dimethylethyl]-2,4,8,10-tetraoxaspiro [5.5]undecane, N,N'-bis[3',5'-di-t-butyl-4'-hydroxyphenyl)propionyl]hydrazine and N,N'-bis[3-(3',5'-di-t-butyl-4'-hydroxyphenyl)propionyl] hexamethylenediamine.

Examples of the preferred phosphorous antioxidant include the followings, and a mixture of two or more kinds of them can also be used:

tris(nonylphenyl)phosphite, tris (2,4-di-t-butylphenyl) phosphite, distearyl pentaerythritol diphosphite, bis(2,4-di-t-butylphenyl)pentaerythritol diphosphite, bis(2,4-di-t-butyl-6-methylphenyl)pentaerythritol disphosphite, bis(2,6-di-t-butyl-4-methylphenyl)pentaerythritol diphosphite, tetrakis(2,4-di-t-butylphenyl)-4,4'-diphenylenediphosphite, 2,2'-methylenebis(4,6-di-t-butylphenyl) 2-ethylhexyl phosphite, 2,2'-ethylidenebis(4,6-di-t-butylphenyl) fluorophosphite, bis(2,4-di-t-butyl-6-methylphenyl) ethylphosphite, 2-(2,4,6-tri-t-butylphenyl)-5-ethyl-5-butyl-1,3,2-oxaphospholinane and 2,2',2"-nitrilo[triethyl-tris(3,3',5,5'-tetra-t-butyl-1,1'-biphenyl-2,2'-diyl)phosphite.

Examples of the preferred ultraviolet absorber include the followings, and a mixture of two or more kinds of them can also be used:

phyenyl salicylate, 4-t-butylphenyl salicylate, 2,4-di-t-butylphenyl 3',5'-di-t-butyl-4'-hydroxybenzoate, 4-t-octylphenyl salycilate, 2,4-dihydroxybenzophenone, 2-hydroxy-4-methoxybenzophenone, 2-hydroxy-4-octoxybenzophenone, 2,2'-dihydroxy-4-methoxybenzophenone, bis(5-benzoyl-4-hydroxy-2-methoxyphenyl)methane, 2,2',4,4'-tetrahydroxybenzophenone, 2-(2-hydroxy-5-methylphenyl)benzotriazole, 2-(2-hydroxy-5-methylphenyl)benzotriazole, 2-(3',5'-di-t-butyl-2'-hydroxyphenyl)benzotriazole, 2-(5'-t-butyl-2'-hydroxyphenyl)benzotriazole, 2-(2'-hydroxy-5'-t-octylphenyl)benzotriazole, 2-(3-t-butyl-2-hydroxy-5-methylphenyl)-5-chlorobenzotriazole, 2-(3'-s-butyl-2'-hydroxy-5'-t-butylphenyl)benzotriazole, 2-(2'-hydroxy-4'-octyloxyphenyl)benzotriazole, 2-(3',5'-di-t-amyl-2'-hydroxyphenyl)benzotriazole and 2-[2'-hydroxy-3',5'-bis($\alpha$,$\alpha$-dimethylbenzyl)phenyl]-2H-benzotriazole.

Examples of the preferred photo stabilizer include the followings, and a mixture of two or more kinds of them can also be used:

bis(2,2,6,6-tetramethyl-4-piperidyl)sebacate, bis(1,2,2,6,6-pentamethyl-4-piperidyl)sebacate, bis (N-octoxy-2,2,6,6-tetramethyl-4-piperidyl)sebacate, bis(N-benzyloxy-2,2,6,6-tetramethyl-4-piperidyl)sebacate, bis(N-cyclohexyloxy-2,2,6,6-tetramethyl-4-piperidyl)sebacate, bis (1,2,2,6,6-pentamethyl-4-piperidyl) 2-(3,5-di-t-butyl-4-hydroxybenzyl)-2-butylmalonate, bis (1-acryloyl-2,2,6,6-tetramethyl-4-piperidyl) 2,2-bis(3,5-di-t-butyl-4-hydroxybenzyl)-2-butylmalonate, bis(2,2,6,6-tetramethyl-4-piperidyl)succinate, 2,2,6,6-tetramethyl-4-piperidyl methacrylate, 4-[3-(3,5-di-t-butyl-4-hydroxyphenyl) propionyloxy)-1-[2-(3-(3,5-di-t-butyl-4-hydroxyphenyl) propionyloxy)ethyl]-2,2,6,6-tetramethylpiperidine, 2-methyl-2-(2,2,6,6-tetramethyl-4-piperidyl)amino-N-(2,2,6,6-tetarmethyl-4-piperidyl)propionamide, tetrakis(2,2,6,6-tetramethyl-4-piperidyl) 1,2,3,4-butanetetracarboxylate. tetrakis(1,2,6,6-pentamethyl-4-piperidyl) 1,2,3,4-butanetetracarboxylate, mixed esterified product of 1,2,3,4-butanetetracarboxylic acide and 1,2,2,6,6-pentamethyl-4-piperidinol and 1-tridecanol, mixed esterified product of 1,2,3,4-butanetetracarboxylic acid and 2,2,6,6-tetramethyl-4-piperidinol and 1-tridecanol, mixed esterified product of 1,2,3,4-tetracarboxylic acid and 1,2,2,6,6,-pentamethyl-4-piperidinol and 3,9-bis(2-hydroxy-1,1-dimethylethyl)-2,4,8,10-tetraoxaspiro[5,5]undecane, mixed esterified product of 1,2,3,4-butanetetracarboxylic acid and 2,2,6,6-tetarmethyl-4-piperidinol and 3,9-bis(2-hydroxy-1,1-dimethylethyl)-2,4,8,10-tetraoxaspiro[5,5]undecane, polycondensate of dimethyl succinate and 1-(2-hydroxyethyl)-4-hydroxy-2,2,6,6-tetramethylpiperidine, poly[(6-morphonlino-1,3,5-triazin-2,4-diyl)((2,2,6,6-tetramethyl-4-piperidyl)imino) hexamethylene ((2,2,6,6-tetramethyl-4-piperidyl)imino)] and poly[(6-(1,1,3,3-tetramethybutyl)-1,3,5-triazine-2,4-diyl ((2,2,6,6-tetramethyl-4-piperidyl)imino)hexamethylene ((2,2,6,6-tetramethyl-4-piperidyl)imino)].

When the phosphites (I) or other optional additives are formulated in the organic material, any known methods and devices for obtaining a homogeneous mixture can be used. For example, when the organic material is a solid polymer, the phosphites (I) or other additives can be directly dry-blended in the solid polymer. Alternatively, after preparing a mixture of them with a small amount of the polymer, i.e. masterbatch, the masterbatch can also be formulated in the solid polymer. When the organic material is a liquid polymer, the phosphites (I) and other optional additives can be formulated in the polymer solution during or immediately after polymerization in the form of a solution or a dispersion. On the other hand, when the organic material is a liquid such as oil, the phosphites (I) and other optional additives can also be dissolved by direct addition, or the phosphites (I) and other optional additives can also be added in the form of a solution or dispersion in the liquid medium.

The phosphites (I) of the present invention exhibit excellent performance as a stabilizer for various organic materials, particularly thermoplastic resin such as polyolefin. The orgranic material containing this compound is stable to heat deterioration and oxidization deterioration on their production, processing and use.

The following Examples further illustrate the present invention in detail but are not to be construed to limit the scope thereof.

EXAMPLE 1

Production of 2,10-dimethyl-4,8-di-t-butyl-6-[3-(3,5-di-t-butyl-4-hydroxyphenyl)propoxy]-12H-dibenzo[d,g][1,3,2] dioxaphosphosine (compound 1)

In a flask equipped with a thermometer, a stirrer and a condenser, 10.2 g of 2,2'-methylenebis(6-t-butyl-4-methylphenol) and 110 ml of toluene were charged under a nitrogen gas flow. Thereto, 4.1 g of phosphorous trichloride and then 6.7 g of triethylamine were added with stirring, and the resulting mixture was maintained at 80° C. for 8 hours.

After cooling to room temperature, 50 ml of toluene and 8.33 g of 3-(3,5-di-t-butyl-4-hydroxyphenyl)propanol were added. To the resulting mixture, 3.3 g of triethylamine was further added, and then the mixture was maintained at 80° C. for 7 hours.

After cooling to room temperature, the formed hydrochloride of triethylamine was filtered and washed. The filtrate was concentrated and the residue was purified by silica gel chromatograpy to obtain 4.6 g of a white crystal.

Mass spectrinetruc analysis (FD-MS): m/z 632

$^1$H-NMR (CDCl$_3$): 1.41 (s, 18 H), 1.44 (s,18 H), 2.11 (d of d, 2 H), 2.28 (s, 6 H), 2.77 (t, 8 Hz, 2 H), 3.35 (d, 12 H, 1 H), 4.31 (d, 12 H, 1 H), 4.49 (t, 6 Hz, 2 H), 5.02 (s, 1 H, 7.02 (s, 2 H), 7.05 (s, 2 H), 7.09 (s, 2 H)

$^{31}$P-NMR (CDCl$_3$): 130.01 ppm(s)

EXAMPLE 2

Production of 2,4,8,10-tetra-t-butyl-6-[3-(3,5-di-t-butyl-4-hydroxyphenyl)propoxyl]dibenzo[d,f][1,3,2] dioxaphosphepine (compound 2)

According to the same manner as that described in Example 1 except for using 12.3 g of 3,3,',5,5'-tetra-t-butylbiphenyl-2,2'-diol in place of 10.2 g of 2,2'-methylenebis(6-t-butyl-4-methylphenol), 25.3 g of a white crystal was obtained.

Mass spectrometric analysis (FD-MS): m/z 702

$^1$H-NMR (CDCl$_3$): 1.34 (s, 18 H), 1.41 (s,18 H), 1.49 (s, 18 H) , 1.85 (d of d, 2 H), 2.53 (t, 8 Hz, 2 H), 3.83 (t, 7 Hz, 2 H), 5.02 (s, 1 H, 6.92 (s, 2 H), 7.25 (s, 2 H, 7.42 (s, 2 H), $^{31}$P-NMR (CDCl$_3$): 136.6 ppm(s)

EXAMPLE 3

Production of 2,4,8,10-tetra-t-pentyl-6-[3-(3,5-di-t-butyl-4-hydroxyphenyl)propoxyl]-12-methyl-12H-dibenzo [d,g][1,3,2]dioxaphosphosine (compound 3)

In a flask equipped with a thermometer, a stirrer and a condenser, 11.2 g of 2,2'-ethylidenebis(4,$\epsilon$-di-t- pentylphenol) and 100 ml of toluene were charged under a nitrogen gas flow. Thereto, 3.1 g of phosphorous trichloride and then 5.0 g of triethylamine were added with stirring, and the resulting mixture was maintained at 80° C. for 6 hours.

After cooling to room temperature, 60 ml of toluene and 6.0 g of 3-(3,5-di-t-butyl-4-hydroxyphenyl)propanol were added. To the resulting mixture, 2.5 g of triethylamine was further added, and then the mixture was maintained at 80° C. for 6 hours.

After cooling to room temperature, the formed hydrochloride of triethylamine was filtered and washed. The filtrate was concentrated and the residue was purified by silica gel chromatography to obtain 15.6 g of a colorless oily liquid.

Mass spectrometric analysis (FD-MS): m/z 787
$^1$H-NMR (CDCl$_3$) 0.6 (m, 12 H), 1.26 (s,12 H), 1.36 (s, 12 H) , 1.45 (s, 18 H), 1.64 (d, 3 H, 1.68 (q, 4 H, 1.82 (t, 7 Hz, 2 H), 2.12 (t, 7 Hz, 4 H), 2.79 (d of d, 2 H, 4.51 (t, 2 H), 4.91 (q, 1 H), 6.11 (s, 1 H), 7.05 (s, 2 H), 7.07 (s, 2 H)
$^{31}$P-NMR (CDCl$_3$): 128.8 ppm(s)

EXAMPLE 4

Production of 2,10-dimethyl-4,8-di-t-butyl-6-[3-(3,5-di-t-butyl-4-hydroxyphenyl)propionyloxyl]-12H-dibenzo[d,g][1,3,2]dioxaphosphosine (compound 4)

In a flask equipped with a thermometer, a stirrer and a condenser, 13.6 g of 2,2'-ethylanebis(6,t-butyl-4-methylphenol) and 100 ml of toluene were charged under a nitrogen gas flow. Thereto, 5.5 g of phosphorous trichloride and then 8.9 g of triethylamine were added with stirring, and the resulting mixture was maintained at 80° C. for 7 hours.

After cooling to room temperature, 50 ml of toluene and 11.1 g of 3-(3,5-di-t-butyl-4-hydroxyphenyl)propionic acid were added. To the resulting mixture, 4.5 g of triethylamine was further added, and then the mixture was maintained at 80° C. for 15 hours.

After cooling to room temperature, the formed hydrochloride of triethylamine was filtered and washed. The filtrate was concentrated and the residue was purified by silica gel chromatography to obtain 8.7 g of a white crystal.

Mass spectrometric analysis (FD-MS): m/z 646
$^1$H-NMR (CDCl$_3$) 1.36 (s, 18 H), 1.44 (s, 18 H), 2.29 (s, 6 H) , 2.8 (t, 2 H), 2.9 (t, 2 H, 3.57 (d, 13 Hz 1 H), 4.13 (d, 12 Hz, 1 H), 5.10 (s, 1 H), 7.03 (s, 4 H, 7.08 (s, 2 H)
$^{31}$P-NMR (CDCl$_3$): 130.6 ppm(s)

EXAMPLE 5

Production of 2,4,8,10-tetra-t-pentyl-6-[3-(3,5-di-t-butyl-4-hydroxyphenyl)propionyloxyl]-12-methyl-12H-dibenzo[d,g][1,3,2]dioxaphosphosine (compound 5)

In a flask equipped with a thermometer, a stirrer and a condenser, 17.8 g of 2,2'-ethylidenebis(4,6,-di-t-pentylphenol) and 150 ml of toluene were charged under a nitrogen gas flow. Thereto, 4.9 g of phosphorous trichloride and then 7.7 g of triethylamine were added with stirring, and the resulting mixture was maintained at 80° C. for 4 hours.

After cooling to room temperature, 50 ml of toluene and 10 g of 3-(3,5-di-t-butyl-4-hydroxyphenyl)propionic acid were added. To the resulting mixture, 3.8 g of triethylamine was further added, and then the mixture was maintained at 80° C. for 5 hours.

After cooling to room temperature, the formed hydrochloride of triethylamine was filtered and washed. The filtrate was concentrated and the residue was purified by silica gel chromatography to obtain 20 g of a colorless oily liquid.

Mass spectrometric analysis (FD-MS): m/z 801
$^1$H-NMR (CDCl$_3$) 0.6 (t, 12 H), 1.2–1.4 (m, 42 H), 1.6 (d, 3 H) , 1.7–1.8 (m, 8 H), 2.9 (t, 2 H, 3.0 (t, 2 H), 4.9 (q, 1 H), 5.1 (s, 1 H), 7.05 (s, 4 H, 7.3 (s, 2 H)
$^{31}$P-NMR (CDCl$_3$): 132 ppm(s)

EXAMPLE 6

Production of 2,4,8,10-tetra-t-butyl-6-[3-(3,5-di-t-butyl-4-hydroxyphenyl)propionyloxyl]-dibenzo[d,f][1,3,2]dioxaphosphosine (compound 6)

In a flask equipped with a thermometer, a stirrer and a condenser, 14.8 g of 3,3',5,5'-tetra-t-butylbiphenyl-2,2'-diol and 150 ml of toluene were charged under a nitrogen gas flow. Thereto, 4.9 g of phosphorous trichloride and then 7.7 g of triethylamine were added with stirring, and the resulting mixture was maintained at 80° C. for 4 hours.

After cooling to room temperature, 50 ml of toluene and 10 g of 3-(3,5-di-t-butyl-4-hydroxyphenyl)propionic acid were added. To the resulting mixture, 3.8 g of triethylamine was further added, and then the mixture was maintained at 80° C. for 5 hours.

After cooling to room temperature, the formed hydrochloride of triethylamine was filtered and washed. The filtrate was concentrated and the residue was purified by silica gel chromatography to obtain 21.7 g of a white crystal.

Mass spectrometric analysis (FD-MS): m/z 716
$^1$H-NMR (CDCl$_3$) 1.4–1.6 (m, 54 H), 2.65 (t, 2 H), 3.87 (t, 2 H) , 5.07 (s, 1 H), 6.94 (s, 2 H, 7.17 (s, 2 H), 7.45 (s, 2 H)
$^{31}$P-NMR (CDCl$_3$): 135 ppm(s)

EXAMPLE 7

Production of 2,,10-dimethyl-4,8-di-t-butyl-6-(3,5-di-t-butyl-4-hydroxybenzoyloxy)-12H-dibenzo[d,g][1,3,2]dioxaphosphosine (compound 7)

In a flask equipped with a thermometer, a stirrer and a condenser, 17 g of 2,2'-methylenebis(6-t-butyl-4-methylphenol) and 180 ml of toluene were charged under a nitrogen gas flow. Thereto, 6.9 g of phosphorous trichloride and then 10.6 g of triethylamine were added with stirring, and the resulting mixture was maintained at 80° C. for 3 hours.

After cooling to room temperature, 100 ml of toluene and 12.5 g of 3,5-di-t-butyl-4-hydroxybenzoic acid were added. To the resulting mixture, 5.2 g of triethylamine was further added, and then the mixture was maintained at 80° C. for 10 hours.

After cooling to room temperature, the formed hydrochloride of triethylamine was filtered and washed. The filtrate was concentrated and the residue was purified by silica gel chromatography to obtain 11.9 g of a white crystal.

Mass spectrometric analysis (FD-MS): m/z 618
$^1$H-NMR (CDCl$_3$) 1.38 (s, 18 H), 1.43 (s, 18 H), 2.29 (s, 6 H) , 3.80 (d, 14 Hz, 1 H), 4.11 (d, 14 Hz, 1 H), 5.77 (s, 1 H), 7.02 (s, 2 H), 7.07 (s, 2 H), 7.89 (s, 2 H)
$^{31}$P-NMR (CDCl$_3$): 128.0 ppm(s)

EXAMPLE 8

Production of 2,4,8,10-tetra-t-butyl-6-(3,5-di-t-butyl-4-hydroxyphenylbenzoyloxy-12-methyl-12H-dibenzo[d,g][1,3,2]dioxaphosphosine (compound 8)

In a flask equipped with a thermometer, a stirrer and a condenser, 21.9 g of 2,2'-ethylidenebis(4,6-di-t-butylphenol) and 180 ml of toluene were charged under a nitrogen gas flow. Thereto, 6.9 g of phosphorous trichloride and then 10.6 g of triethylamine were added with stirring, and the resulting mixture was maintained at 80° C. for 3 hours.

After cooling to room temperature, 100 ml of toluene and 12.5 g of 3,5-di-t-butyl-4-hydroxybenzoic acid were added. To the resulting mixture, 5.2 g of triethylamine was further added, and then the mixture was maintained at 80° C. for 10 hours.

After cooling to room temperature, the formed hydrochloride of triethylamine was filtered and washed. The filtrate was concentrated and the residue was purified by silica gel chromatography to obtain 5.5 g of a white crystal.

Mass spectrometric analysis (FD-MS): m/z 717

$^1$H-NMR (CDCl$_3$) 1.32 (s, 18 H), 1.43 (s, 18 H), 1.50 (s, 18 H) , 1.64 (d, 8 Hz, 3 H), 2.29 (s, 6 H, 5.04 (q, 1 H), 5.82 (s, 1 H), 7.25 (s, 2H), 7.42 (s, 2H), 8.12 (s, 2H)

$^{31}$P-NMR (CDCl$_3$): 132.6 ppm(s)

EXAMPLE 9

Production of 2,4,8,10-tetra-t-butyl-6-[3-(3-methyl-4-hydroxy-5-t-butyphenyl)propoxyl]dibenzo[d,f][1,3,2] dioxaphosphosine (compound 9)

In a flask equipped with a thermometer, a stirrer and a condenser, 12 g of 3,3',5,5'-tetra-t-butylbiphenyl-2,2'-diol and 200 ml of toluene were charged under a nitrogen gas flow. Thereto, 4 g of phosphorous trichloride and then 6.5 g of triethylamine were added with stirring, and the resulting mixture was maintained at 80° C. for 4 hours.

After cooling to room temperature, 50 ml of toluene and 6.5 g of 3-(3-t-butyl-4-hydroxy-5-methylphenyl)propanol were added. To the resulting mixture, 3.3 g of triethylamine was added, and then the mixture was maintained at 80° C. for 4 hours.

After cooling to room temperature, the formed hydrochloride of triethylamine was filtered and washed. The filtrate was concentrated and the residue was purified by silica gel chromatography to obtain a white crystal.

Mass spectrometric analysis (FD-MS): m/z 660

$^1$H-NMR (CDCl$_3$) 1.34 (s, 18 H), 1.37 (s, 9 H), 1.49 (s, 18 H) , 1.84 (m, 2 H), 2.18 (s, 3 H, 2.51 (t, 2 H), 3.81 (dt, 2 H), 4.59 (s, 1H), 6.76 (s, 1H), 6.89 (s, 1H), 7.16 (d, 2H)

$^{31}$P-NMR (CDCl$_3$): 136.4 ppm(s)

EXAMPLE 10

Production of 2,10-dimethyl-4,8-di-t-butyl-6-[3-(3-methyl-4-hydroxy-5-t-butylphenyl)propoxy]-12H-dibenzo [d,g][1,3,2]dioxaphosphosine (compound 10)

According to the same manner as that described in Example 9 except for using 10 g of 2,2'-methylenebis(6-t-butyl-4-methyphenol) in place of 3,3',5,5'-tetra-t-butylphenyl-2,2'-diol, a white crystal was obtained.

Mass spectrometric analysis (FD-MS): m/z 590

EXAMPLE 11

Production of 2,4,8,10-tetra-t-butyl-6-[3-(3,5-di-t-butyl-4-hydroxyphenyl)propoxy]-12H-dibenzo[d,g][1,3,2] dioxaphosphosine (compound 11)

According to the same manner as that described in Example 9 except for using 12 g of 2,2'-methylenebis(4,6-di-t-butylphenol) in place of 3,3',5,5'-tetra-t-butylbiphenyl-2,2'diol and using 7.5 g of 3-(3,5-di-t-butyl-4-hydroxyphenyl)propanol in place of 3-(3-t-butyl-4-hydroxy-5-methylphenyl)propanol, a white crystal was obtained.

Mass spectrometric analysis (FD-MS): m/z 717

EXAMPLE 12

Production of 2,10-diethyl-4,8-di-t-butyl-6-[3-(3,5-di-t-butyl-4-hydroxyphenyl)propoxy]-12H-dibenzo[d,g][1,3,2] dioxaphosphosine (compound 12)

In a flask equipped with a thermometer, a stirrer and a condenser, 12 g of 2,2'-methylenebis(6-t-butyl-4-ethylphenol) and 200 ml of toluene were charged under a nitrogen gas flow. Thereto, 4.5 g of phosphorous trichloride and then 7.2 g of triethylamine were added with stirring, and the resulting mixture was maintained at 80° C. for 4 hours.

After cooling to room temperature, 50 ml of toluene and 8.6 g of 3-(3,5-di-t-butyl-4-hydroxyphenyl)propanol were added. To the resulting mixture, 3.6 g of triethylamine was added, and then the mixture was maintained at 80° C. for 4 hours.

After cooling to room temperature, the formed hydrochloride of triethylamine was filtered and washed. The filtrate was concentrated and the residue was purified by silica gel chromatograpy to obtain a white crystal.

Mass spectrometric analysis (FD-MS): m/z 661

EXAMPLE 13

Production of 2,4,8,10-tetra-t-butyl-6-[2,2-dimethyl-3(3-t-butyl-4-hydroxy-5-methylphenyl)propoxy]-dibenzo[d,f] [1,3,2]dioxaphosphosine (compound 13)

In a flask equipped with a thermometer, a stirrer and a condenser, 13 g of 3,3',5,5'-tetra-t-butylbiphenyl-2,2'-diol and 200 ml of toluene were charged under a nitrogen gas flow. Thereto, 4.3 g of phosphorous trichloride and then 4.3 g of triethylamine were added with stirring, and the resulting mixture was maintained at 80° C. for 4 hours.

After cooling to room temperature, 50 ml of toluene and 7.9 g of 2,2-dimethyl-3-(3,5-di-t-butyl-4-hydroxyphenyl) propanol were added. To the resulting mixture, 3.5 g of triethylamine was added, and then the mixture was maintained at 80° C. for 4 hours.

After cooling to room temperature, the formed hydrochloride of triethylamine was filtered and washed. The filtrate was concentrated and the residue was purified by silica gel chromatograpy to obtain a white crystal.

Mass spectrometric analysis (FD-MS): m/z 688

EXAMPLE 14

Thermal stability test of polypropylene
[Formulation]
Polypropylene (block) 100 Parts by weight
Calcium stearate 0.05 Parts by weight
Stabilizer to be tested 0.05 Parts by weight
C-1: Compound 1 (produced in Example 1)
C-2: Compound 2 (produced in Example 2)
C-3: Compound 3 (produced in Example 3)
C-4: Compound 4 (produced in Example 4)
C-5: Compound 5 (produced in Example 5)
C-6: Compound 6 (produced in Example 6)
C-7: Compound 7 (produced in Example 7)
C-8: Compound 8 (produced in Example 8)
C-9: Compound 9 (produced in Example 9)
C-10: Compound 10 (produced in Example 10)
C-11: Compound 11 (produced in Example 11)
C-12: Compound 12 (produced in Example 12)
C-13: Compound 13 (produced in Example 13)
M-1: mixture of compound 9 (produced in Example 9) and tri-i-propanolamine in weight ratio of 99:1

P-1: 2,10-dimethyl-4,8-di-t-butyl-6-{2-[3-(3-t-butyl-4-hydroxy-5-methylphenyl)propionyloxy]ethoxy}-12H-dibenzo[d,g][1,3,2]dioxaphosphosine P-2: 2,4,8,10-tetra-t-pentyl-6-{2-[3-(3,5-di-t-butyl-4-hydroxyphenyl)propionyloxy]ethoxy}-12-methyl-12H-dibenzo[d,g][1,3,2]dioxaphosphosine Using a 30 mm φ single screw extruder, the above formulation was re-pelleted at 250° C. MFR (g/minute) of the resulting pellets were measured at 250° C. under a load of 2160 g for a detention time of 5 minutes by using a melt indexer. The results are shown in Table 1. The smaller the MFR, the better the processing stability.

TABLE 1

| | Example | | | | | | | |
|---|---|---|---|---|---|---|---|---|
| | 1 | 2 | 3 | 4 | 5 | 6 | 7 | 8 |
| Compound to be tested | C-1 | C-2 | C-3 | C-4 | C-5 | C-6 | C-7 | C-8 |
| Processing stability | 19.9 | 20.2 | 20.9 | 18.7 | 21.2 | 21.0 | 20.0 | 20.6 |

| | Example | | | | | |
|---|---|---|---|---|---|---|
| | 9 | 10 | 11 | 12 | 13 | 14 |
| Compound to be tested | C-9 | C-10 | C-11 | C-12 | C-13 | M-1 |
| Processing stability | 18.6 | 18.3 | 19.0 | 19.2 | 18.3 | 18.5 |

| | Comparative Example | | |
|---|---|---|---|
| | 1 | 2 | 3 |
| Compound to be tested | — | P-1 | P-2 |
| Processing stability | 29.4 | 22.0 | 22.5 |

EXAMPLE 15

Thermal stability test of straight-chain low-density polyethylene

| Unstabilized straight-chain low-density polyethylene | 100 Parts by weight |
|---|---|
| Hydrotalcite | 0.1 Parts by weight |
| Compound to be tested | 0.15 Parts by weight |

C-1: Compound 1 (produced in Example 1)
C-2: Compound 2 (produced in Example 2)
C-3: Compound 3 (produced in Example 3)
C-4: Compound 4 (produced in Example 4)
C-5: Compound 5 (produced in Example 5)
C-6: Compound 6 (produced in Example 6)
C-7: Compound 7 (produced in Example 7)
C-8: Compound 8 (produced in Example 8)
C-9: Compound 9 (produced in Example 9)
M-1: mixture of compound 9 (produced in Example 9) and tri-i-propanolamine in weight ratio of 99:1
P-1: 2,10-dimethyl-4,8-di-t-butyl-6-{2-[3-(3-t-butyl-4-hydroxy-5-methylphenyl)propionyloxy]ethoxy}-12H-dibenzo[d,g][1,3,2]dioxaphosphosine
P-2: 2,4,8,10-tetra-t-pentyl-6-{2-[3-(3,5-di-t-butyl-4-hydroxyphenyl)propionyloxy]ethoxy}-12-methyl-12H-dibenzo[d,g][1,3,2]dioxaphosphosine Using a 30 mm φ single screw extruder, the above formulation was re-pelleted at 250° C. The resulting pellets were kneaded under a nitrogen atmosphere at 240° C. at 100 rpm using a laboplast mill. The time required for the torque value to become maximum (gelled-up time, minute) was measured. The results are shown in Table 2. The longer the gelled-up time, the better the processing stability because the crosslinking on kneading is inhibited.

TABLE 2

| | Example | | | | | |
|---|---|---|---|---|---|---|
| | 1 | 2 | 3 | 4 | 5 | 6 |
| Compound to be tested | C-2 | C-3 | C-4 | C-5 | C-6 | C-7 |
| Processing stability | 26.0 | 22.5 | 27.0 | 26.0 | 23.0 | 32.0 |

| | Example | | | Comparative Example | | |
|---|---|---|---|---|---|---|
| | 7 | 8 | 9 | 1 | 2 | 3 |
| Compound to be tested | C-8 | C-9 | M-1 | — | P-1 | P-2 |
| Processing stability stability | 26.0 | 31.0 | 31.0 | 5.0 | 16.5 | 17.0 |

EXAMPLE 16

NOx discloration resistance test of straight-chain low-density polyethylene

[Formulation]

| Unstabilized straight-chain low-density polyethylene | 100 Parts by weight |
|---|---|
| Hydrotalcite | 0.1 Parts by weight |
| Phenol compound* | 0.15 Parts by weight |
| Stabilizer to be tested | 0.1 Parts by weight |

*Phenol compound: n-octadecyl-3-(3,5-di-t-butyl-4-hydroxyphenyl propionate.

Using 30 mm φ single screw extruder, the above formulation was re-pelletized at 250° C. The resulting pellets were molded into a sheet at 250° C. by using a oz injection molding machine.

The resulting sheet was exposed to a 3% NOx gas for 2 hours and a YI value before and after exposure was measured, respectively. A difference ΔYI between them is shown in Table 3. The smaller the ΔYI, the better the NOx Discoloration resistance because the degree of discoloration due to the NOx gas is small.

TABLE 3

| | Example | | | | | | |
|---|---|---|---|---|---|---|---|
| | 1 | 2 | 3 | 4 | 5 | 6 | 7 |
| Compound to be tested | C-1 | C-2 | C-3 | C-4 | C- | C- 7 | C-9 |
| Δ YI | 7.2 | 7.5 | 8.1 | 10.1 | 10.9 | 10.6 | 7.3 |

| | Example | | | Comparative Example | |
|---|---|---|---|---|---|
| | 8 | 9 | 10 | 1 | 2 |
| Compound to be tested | C-10 | C-11 | C-12 | P-1 | P-3 |
| ΔYI | 6.7 | 6.3 | 10.7 | 12.7 | 13.6 |

EXAMPLE 17

[Formulation]

| Unstabilized nylon 6 | 100 Parts by weight |
| Stabilizer to be tested | 1 Part by weight |

C-1: Compound 1 (produced in Example 1)
C-2: Compound 2 (produced in Example 2)
C-9: Compound 9 (produced in Example 9)
C-10: Compound 10 (produced in Example 10)
C-13: Compound 13 (produced in Example 13)
P-3: 2,4,8,10-tetra-t-butyl-6-{2-[3-(3-t-butyl-4-hydroxy-5-methylphenyl)propionyloxy]ethoxy}-dibenzo[d,f,][1,3,2]dioxaphosphepine The above formulation was dry blended and then kneaded at 300° C. at 80 rpm for 5 minutes by using a laboplast mill. A torque value after the 5 minutes kneading is shown in Table 4. Since nylon 9 is decomposed by deterioration and the torque value is reduced, the higher the torque value after the 5 minutes kneading, the better the processing stability.

TABLE 4

|  | Example | | | | | Comparative Example | |
| --- | --- | --- | --- | --- | --- | --- | --- |
|  | 1 | 2 | 3 | 4 | 5 | 1 | 2 |
| Compound to be tested | C-1 | C-2 | C-9 | C-10 | C-13 | — | P-3 |
| Torque value (kgf) | 56 | 40 | 42 | 54 | 42 | 22 | 33 |

We claim:
1. A phosphite represented by the formula (I):

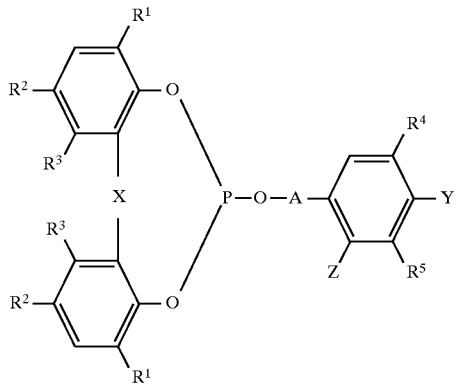

wherein $R^1$, $R^2$, $R^4$ and $R^5$ each independently represent hydrogen atom, an alkyl group having 1 to 8 carbon atoms, a cycloalkyl group having 5 to 8 carbon atoms, an alkylcycloalkyl group having 6 to 12 carbon atoms, an aralkyl group having 7 to 12 carbon atoms or a phenyl group; $R^3$ represents hydrogen atom or an alkyl group having 1 and 8 carbon atoms; X represents a direct bond, sulfur atom, or a —$CHR^6$ group in which $R^6$ represents hydrogen atom, an alkyl group having 1 to 8 carbon atoms or a cycloalkyl group having 5 to 8 carbon atoms; A represents an alkylene group having 2 to 8 carbon atoms or a *—$COR^7$— group in which $R^7$ represents a direct bond or an alkylene group having 1 to 8 carbon atoms, and * represents the bonds to the oxygen; and one of Y and Z represents a hydroxyl group, an alkoxy group having 1 to 8 carbon atoms or an aralkyloxy group having 7 to 12 carbon atoms and the other one represents hydrogen atom or an alkyl group having 1 to 8 carbon atoms.

2. A process for producing the phosphites according to claim 1 which comprises reacting a bisphenol represented by the general formula (II):

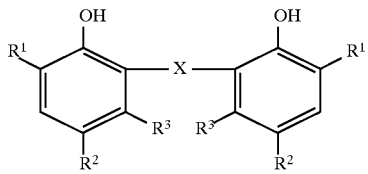

wherein $R^1$, $R^2$, $R^3$ and X are the same as defined in claim 1 and phosphorous trihalide with an hydroxyl compound represented by the general formula (III):

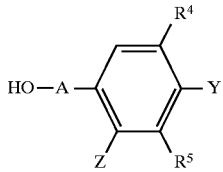

wherein $R^4$, $R^5$, A, Y and Z are the same as defined in claim 1.

3. A stabilizer for an organic material which comprises the phosphite according to claim 1 as an active ingredient.

4. A stabilizer according to claim 3 wherein the organic material is a thermoplastic resin.

5. A stabilizer according to claim 3 wherein the organic material is a polyolefine or an engineering resin.

6. A method for stabilizing an organic material which comprises incorporating the phosphite according to claim 1 in the organic material.

7. A method for stabilizing an organic material according to claim 6 wherein the organic material is a thermoplastic resin.

8. A method for stabilizing an organic material according to claim 6 wherein the organic material is a polyolefine or an engineering resin.

9. A stabilized organic material which comprises the phosphite according to claim 1 and an organic material.

10. A stabilized organic material according to claim 9 wherein the orgainc material is a thermoplastic resin.

11. A stabilized organic material according to claim 9 wherein the organic material is a polyolefine or an engineering resin.

* * * * *